United States Patent [19]
Ashton et al.

[11] Patent Number: 5,387,208
[45] Date of Patent: Feb. 7, 1995

[54] ABSORBENT CORE HAVING IMPROVED DRY/WET INTEGRITY

[75] Inventors: Gregory Ashton, Markham, Canada; John T. Cooper, West Chester, Ohio; Craig A. Hawkins, Toronto, Canada

[73] Assignee: The Procter & Gamble Co., Cincinnati, Ohio

[21] Appl. No.: 97,634

[22] Filed: Jul. 26, 1993

[51] Int. Cl.⁶ .................. A61F 13/15; A61F 13/20
[52] U.S. Cl. .................... 604/378; 604/358; 604/366; 604/368; 604/370; 604/372; 604/384; 604/385.1
[58] Field of Search .............. 604/358, 365, 366, 370, 604/372, 374, 375, 378, 379, 380, 383, 384, 385.1

[56] References Cited

U.S. PATENT DOCUMENTS

| | | |
|---|---|---|
| 3,911,173 | 10/1975 | Sprague, Jr. . |
| 4,195,634 | 4/1980 | DiSalvo et al. . |
| 4,522,863 | 6/1985 | Keck et al. . |
| 4,526,577 | 7/1985 | Schmidt, Jr. et al. ............ 604/366 |
| 4,573,986 | 3/1986 | Minetola et al. ............ 604/366 |
| 4,673,402 | 6/1987 | Weisman et al. . |
| 4,710,185 | 12/1987 | Sneyd et al. . |
| 4,785,996 | 11/1978 | Ziecker et al. . |
| 4,806,408 | 2/1989 | Pierre et al. ............ 428/76 |
| 4,842,666 | 6/1989 | Werenicz . |
| 4,891,249 | 1/1990 | McIntyre . |
| 5,024,667 | 6/1991 | Malcolm et al. . |
| 5,137,537 | 8/1992 | Herron et al. . |
| 5,145,689 | 9/1992 | Allen et al. . |
| 5,147,345 | 9/1992 | Young et al. ............ 604/378 |
| 5,151,092 | 9/1992 | Buell et al. . |
| 5,217,445 | 6/1993 | Young et al. . |
| 5,248,309 | 9/1993 | Serbiak et al. ............ 604/378 |

FOREIGN PATENT DOCUMENTS

| | | | |
|---|---|---|---|
| 2255720 | 11/1992 | United Kingdom .......... | 604/378 |
| 8605089 | 9/1986 | WIPO .......... | 604/358 |
| WO91/11163 | 8/1991 | WIPO . | |
| WO93/11726 | 6/1993 | WIPO . | |

Primary Examiner—Randall L. Green
Assistant Examiner—P. Zuttarelli
Attorney, Agent, or Firm—Loretta J. Henderson; Steven W. Miller; Bart S. Hersko

[57] ABSTRACT

Disclosed is an absorbent article having a liquid pervious topsheet, a liquid impervious backsheet joined to the topsheet, and an absorbent core positioned therebetween, in which the absorbent core is enveloped by a primary core integrity layer comprising a continuous mesh of meltblown material which is joined to the topsheet. The primary core integrity layer is particularly useful for improving the wet integrity of absorbent cores comprising an upper acquisition/distribution layer and a lower storage layer.

16 Claims, 3 Drawing Sheets

ABSORBENT CORE HAVING IMPROVED DRY/WET INTEGRITY

FIELD OF THE INVENTION

The present invention relates to absorbent articles, e.g., diapers, incontinence garments, feminine hygiene articles, and the like, having absorbent cores with improved integrity. More particularly, the present invention relates to such absorbent articles which comprise absorbent cores which are enveloped by a continuous mesh of meltblown material to impart dry, and particularly wet, integrity to the absorbent core and article. The invention is particularly useful for thin absorbent articles in which the absorbent core comprises an acquisition/distribution layer and a storage layer.

BACKGROUND OF THE INVENTION

Absorbent articles such as diapers which employ relatively thin absorbent cores and which are, therefore, relatively thin products, are desired for numerous reasons. For example, thinner diapers are less bulky to wear and fit better under clothing. They are also more compact in the package, making the diapers easier for the consumer to carry and store. Compactness in packaging also results in reduced distribution costs for the manufacturer and distributor.

The improvement in absorbency provided by incorporation of absorbent gelling materials in absorbent cores has permitted the realization of relatively thin absorbent articles. For example, an absorbent structure wherein hydrogel-forming materials in particulate form are incorporated into fibrous webs is disclosed in Weisman et al.; U.S. Pat. No. 4,610,678; issued Sep. 9, 1986.

Another absorbent core configuration which is useful for use as the absorbent structure in relatively thin absorbent articles is disclosed in U.S. Pat. No. 4,765,780, issued Aug. 23, 1988 to Angstadt. This patent discloses absorbent articles, such as diapers, which have a two layer absorbent core configuration wherein the core comprises an upper primary layer and a lower dusting layer. The primary layer is an airlaid web of hydrophilic fiber material with a substantial amount of absorbent gelling material admixed therewith. The dusting layer comprises hydrophilic fiber material and, preferably, contains no absorbent gelling material.

Another absorbent core configuration is disclosed in Weisman et al., U.S. Pat. No. 4,673,402, issued Jun. 16, 1987. This patent discloses absorbent articles having a dual layer absorbent core. In the dual layer configuration, the core comprises an upper primary layer which is an airlaid web of hydrophilic fiber material, optionally with a small amount of polymeric gelling agent particles admixed therewith. The core also comprises an underlying insert layer which is an airlaid mixture of hydrophilic fiber material and a substantial amount of polymeric gelling agent particles. This insert layer is generally positioned toward the front of the absorbent article such that more than half of the polymeric gelling agent material in the article is found in the front half thereof. Absorbent articles having the particular dual layer configuration of U.S. Pat. No. 4,673,402 can be prepared in the form of especially thin, highly effective, low leakage diaper products.

More recently, absorbent structures have been suggested to provide improved fluid acquisition and distribution in absorbent cores. For example, U.S. Pat. No. 4,935,022, issued Jun. 19, 1990 to Lash et al., discloses disposable absorbent articles comprising a layered absorbent core comprising an upper layer of stiffened, twisted, curled cellulose fibers and from about 3% to 15% by weight, of large particle absorbent gelling material; and a lower layer of stiffened, twisted, curled cellulose fibers and from about 15% to 60%, by weight, of absorbent gelling material. The upper layer serves the principal purpose of acquisition and distribution of bodily fluid discharges. The stiffened, twisted, curled fibers are highly beneficial in this regard. The lower layer is principally for fluid storage.

U.S. Pat. No. 5,217,445, issued to Young et al. on Jun. 8, 1993 discloses absorbent cores comprising an acquisition/distribution layer comprising a web of from about 50% to 100% of chemically stiffened cellulosic fibers and from 0% to about 50% of a binding means. Preferred stiffened fibers are intrafiber crosslinked, the crosslinking occurring while the fibers are in a relatively dehydrated, defibrated, twisted, curled condition. Suitable stiffening agents include polycarboxylates, and are described along with a process of making the stiffened fibers, in U.S. Pat. No. 5,137,537, issued to Herron et al. on Aug. 11, 1992.

Although the foregoing structures provide improved absorbency when incorporated into absorbent articles, it has been found that such cores tend to suffer from absorbent core slumping, cracking (i.e., breaking), and/or roping in processing, storage, and/or use. As a result, the absorption characteristics of the absorbent core are decreased such that leakage of the article incorporating the same occurs. This tendency to slump, crack, and/or rope is more likely as the absorbent core becomes thinner, for example, in the foregoing constructions incorporating absorbent gelling material and/or stiffened, twisted, curled cellulosic fibers. Thin constructions particularly suffer from breakage and slumping which are believed to be due to the presence of stiffened, twisted, curled cellulosic fibers, a relatively high absorbent gelling material concentration, and/or the force typically used in packaging of the absorbent article. Breakage tends to occur along the fold lines typically imparted for packaging of the absorbent articles (e.g., in the crotch region). When such breakage occurs, the transport of fluids throughout the absorbent core is impeded. For example, where substantial breakage occurs along the crotch fold line, the rear portion of the absorbent article tends to be substantially unavailable for fluid absorption. Thus, when the front portion of the article is saturated to its absorption capacity, leakage may occur.

The tendency to slump, crack and/or rope is particularly exaggerated in absorbent cores incorporating acquisition/distribution components comprising stiffened, twisted, curled cellulose fibers such as described in the foregoing patents. On the one hand, the relatively low density of such components makes the component more likely to lose its integrity. In addition, when this component is wetted, the fibers tend to pull apart (spring back). In addition, the acquisition/distribution component tends to separate and/or slip away from other layers of the absorbent core (e.g., the storage layer) such that fluid transport from the acquisition/distribution layer to such other layers is hindered.

It is known to use glues in absorbent articles to improve absorbent core integrity. For example, U.S. Pat. No. 4,573,986, issued to Minetola et al. on Mar. 4, 1986 discloses garments in which the liquid permeable lamina and absorbent core are bonded together in face to face relation with an open pattern of adhesive. Minetola discloses that particular laminae are adhesively secured together with particular patterns, quantities, and types of adhesives to achieve faster absorbency; less absorbent core slumping, cracking and roping; and increased tensile strength without substantially reducing either the softness or overall absorbency of the garment.

While the art has solved some of the problems related to absorbent core integrity of laminated absorbent articles, it has not solved the problems to the extent nor in the manner of the present invention; particularly with respect to the integrity of thin diaper configurations having a relatively high absorbent gelling material concentration, more particularly such thin diapers incorporating an acquisition/distribution layer such as those incorporating the above described chemically stiffened, twisted, curled cellulosic fibers.

The glues used to bond the absorbent core to a chassis component (i.e., topsheet or backsheet) tend to have inadequate adhesion to the cellulose fibers which are typically used in the absorbent core when the absorbent article is subjected to the dynamic motions of the wearer. As a result, the glue tends to be insufficient to maintain the integrity of the absorbent core when absorbent articles incorporating the same are in use. The loss of adhesion and integrity is particularly exaggerated when the article is wetted. For example, when the absorbent gelling material and cellulose fibers typically incorporated into the absorbent core component expand upon wetting, the forces exerted by the expanding absorbent gelling material and cellulose fibers tend to cause a loss of adhesion between the absorbent gelling material, fibers, and the glue.

In addition, when absorbent core/chassis glues are applied in a spray application to form beads and/or spirals for bonding of the laminae, the bonding is relatively localized. Thus, although the amount of glue is relatively great, this method of application leaves a large portion of the absorbent core surface unbonded and free to move.

It is an object of the present invention to provide an absorbent structure having improved dry and wet integrity. Thus it is an object of the present invention to provide an absorbent structure having a reduced tendency to break, slump, and/or rope while dry or wet. Another object of the present invention is to provide absorbent articles in which the absorbent core is enveloped by a continuous mesh of meltblown material. It is a further object of this invention to provide such absorbent articles wherein the absorbent core can acquire fluid rapidly in the region of discharge and transport the fluid over a relatively large proportion of an absorbent core storage area and, additionally, be capable of effectively acquiring and distributing discharged bodily fluid from second or other successive voiding. It is yet another object of this invention to provide absorbent articles which are capable of meeting the objects described above which are of a relatively thin design.

SUMMARY OF THE INVENTION

The present invention relates to an absorbent article having a liquid pervious topsheet, a liquid impervious backsheet joined to the topsheet, and an absorbent core positioned therebetween, in which the absorbent core is enveloped by a primary core integrity layer, preferably formed of a continuous mesh of meltblown material, to provide improved absorbent core integrity, especially when wet. The primary core integrity layer serves to hold components of the absorbent core in place, especially when wetted, without interfering substantially with fluid transport into and through the absorbent core.

The absorbent core is preferably enveloped by a primary core integrity layer which is joined to a chassis component of the absorbent article, preferably directly joined to the topsheet. The primary core integrity layer imparts structural integrity to the absorbent core without requiring a great amount of material and without significant interference with absorption. The bond between the primary core integrity layer and the chassis component is preferably relatively cohesive and therefore tends to retain its strength in use such that the absorbent core has a reduced tendency to separate from the chassis component(s). In addition, the absorbent core components have a reduced tendency to slip away and/or separate from one another, particularly upon wetting.

In a preferred embodiment, the absorbent core comprises multiple absorbent layers with at least one secondary core integrity layer positioned between one or more of the absorbent layers. In a particularly preferred embodiment, the absorbent core comprises an acquisition/distribution layer, a storage layer, and a tissue layer positioned between the acquisition/distribution layer and the storage layer. The acquisition/distribution layer is preferably formed of stiffened, twisted, curled, intrafiber crosslinked cellulosic fibers. The storage layer is preferably a mixture of absorbent gelling material and cellulosic fibers. The secondary core integrity layer is preferably positioned between the acquisition/distribution layer and the tissue layer.

The primary and secondary core integrity layers are preferably formed from a thermoplastic material, more preferably a hot-melt adhesive such that the core integrity layers can be readily formed on-line during construction of the absorbent article. More preferably, the core integrity layers are formed from a hot-melt, elastomeric adhesive. Elastomeric, hot-melt adhesives tend to be flexible such that there is a reduced tendency for adhesive and/or cohesive failure of the bonds effecting joinder in the article (relative to non-elastomeric adhesives). As a result, the absorbent core has an enhanced tendency to remain in place and to retain its integrity. Most preferably, the core integrity layers are formed from an elastomeric, hot-melt, pressure-sensitive adhesive. The tack of the pressure-sensitive adhesive further reduces the tendency of absorbent core components adjacent the primary or secondary core integrity layers to separate from other absorbent article components, and is particularly effective in reducing slippage/separation of the acquisition/distribution layer from the storage layer.

In a preferred embodiment, both the primary and secondary core integrity layers are formed of strands of hot-melt adhesive having a fiber denier of at least about 60 microns, and further have a basis weight of about 2 to about 8 g/m$^2$.

DESCRIPTION OF PREFERRED EMBODIMENTS

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, training pants, diaper holders and liners, feminine hygiene garments, feminine hygiene products such as sanitary napkins and pantiliners, and the like.

Figure 1:
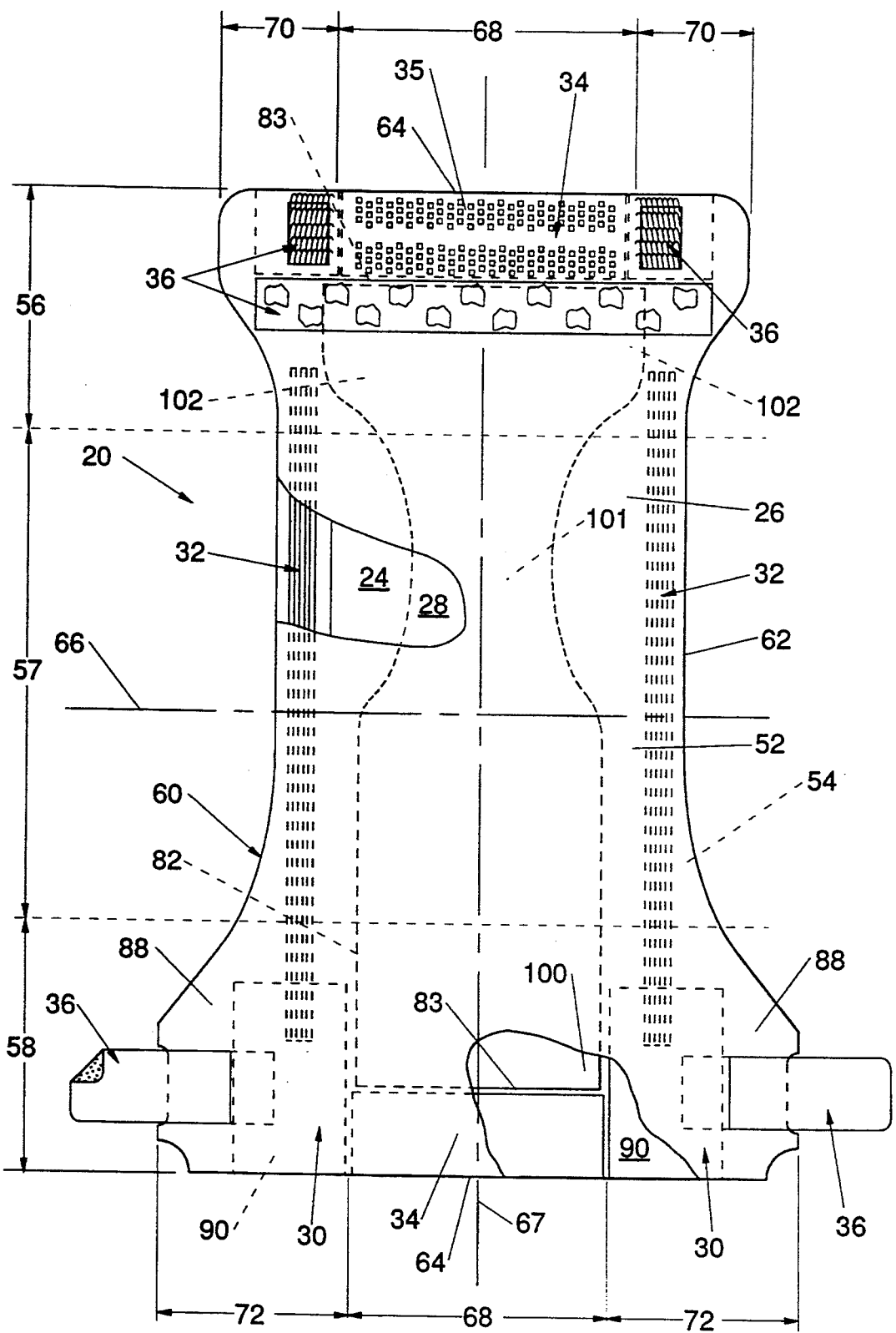
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface, oriented towards the viewer. As shown in FIG. 1, the diaper 20 preferably comprises a liquid pervious topsheet 24; a liquid impervious backsheet 26 joined with the topsheet 24; an absorbent core 28 positioned between the topsheet 24 and the backsheet 26, the absorbent core 28 having a garment facing surface 100, a body facing surface 101, side edges 82, waist edges 83, and ears 102; elasticized side panels 30; elasticized leg cuffs 32; an elastic waist feature 34; and a fastening system generally multiply designated as 36. The diaper 20 is shown in FIG. 1 to have an outer surface 52, an inner surface 54 opposed to the outer surface 52, a first waist region 56, a second waist region 58, a crotch region 57 positioned between the first waist region 56 and second waist region 58, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e., the inner surface 54 generally is formed by at least a portion of the topsheet 24 and other components joined to the topsheet 24). The outer surface 52 comprises that portion of the diaper 20 which is positioned away from the wearer's body (i.e., the outer surface 52 generally is formed by at least a portion of the backsheet 26 and other components joined to the backsheet 26). (As used herein, the portion of the diaper 20 or component thereof which faces the wearer is also referred to as the body facing surface. Similarly, the portion facing away from the wearer is also referred to herein as the garment facing surface.) Both the first waist region 56 and the second waist region 58 comprise a central region 68 and a pair of side panels which typically comprise the outer lateral portions of the waist regions. The side panels positioned in the first waist region 56 are designated 70 while the side panels in the second waist region 58 are designated 72.

FIG. 1 shows a preferred embodiment of the diaper 20 in which the topsheet 24 and the backsheet 26 have length and width dimensions generally larger than those of the absorbent core 28. The elasticized leg cuffs 32 and the backsheet 26 extend beyond the edges of the absorbent core 28 to thereby form the periphery 60 of the diaper 20. While the topsheet 24, the backsheet 26, and the absorbent core 28 may be assembled in a variety of well known configurations, preferred diaper configurations are described generally in U.S. Pat. No. 3,860,003 entitled "Contractible Side Portions for Disposable Diaper" which issued to Buell on Jan. 14, 1975; and U.S. Pat. No. 5,151,092, "Absorbent Article With Dynamic Elastic Waist Feature Having A Predisposed Resilient Flexural Hinge" issued to Buell et al on Sep. 29, 1992; each of which is incorporated herein by reference. Alternatively preferred configurations for disposable diapers herein are also disclosed in U.S. Pat. No. 4,808,178 entitled "Disposable Absorbent Article Having Elasticized Flaps Provided with Leakage Resistant Portions" issued to Aziz et al. on Feb. 28, 1989; U.S. Pat. No. 4,695,278 entitled "Absorbent Article Having Dual Cuffs" issued to Lawson on Sep. 22, 1987; U.S. Pat. No. 4,795,454 entitled "Absorbent Article Having Leakage-Resistant Dual Cuffs," issued to Dragoo on Jan. 3, 1989; U.S. Pat. No. 4,816,025 entitled "Absorbent Article Having a Containment Pocket" issued to Foreman on Mar. 28, 1989; and U.S. Pat. No. 5,026,364 entitled "Absorbent Article Having Unitary Waistcap and Waistband," issued Jun 25, 1991 to Robertson. These patents are incorporated herein by reference.

Figure 2:
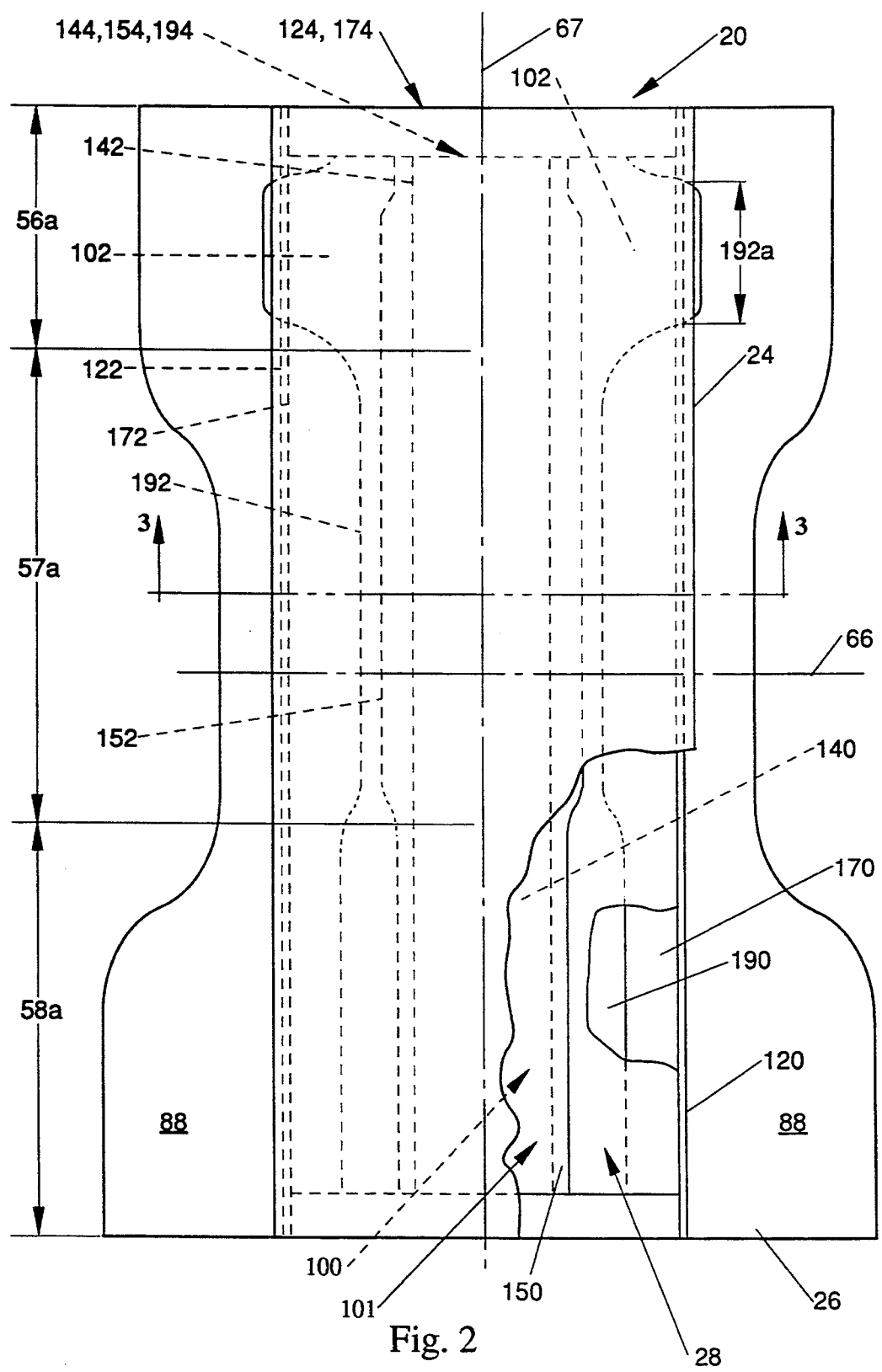
FIG. 2 is a simplified view of the diaper of FIG. 1 but containing a multiple layer absorbent core according to the present invention and having portions thereof cutaway to reveal additional underlying structure, the inner surface of the diaper facing the viewer.

FIG. 2 is a simplified view of diaper 20 as viewed from the opposite, body facing side. In FIG. 2, the elasticized side panels 30; elasticized leg cuffs 32; elastic waist feature 34; and fastening system 36 are removed for simplification.

As shown in FIG. 2, the diaper 20 contains, positioned between topsheet 24 and backsheet 26, a preferred absorbent core 28 comprising a storage layer 190, tissue layer 170, and acquisition/distribution layer 150. As shown in FIG. 2, the absorbent core 28 has a first waist region 56a, a second waist region 58a, and a crotch region 57a. The first waist region 56a is typically positioned at the end of the diaper 20 that would be covering the front of the wearer when the diaper is in use (the second waist region 58a would be at the back of the user).

Referring to FIG. 2, the storage layer 190 has a modified hour-glass shape to provide enhanced fit and reduce in-use leakage. More specifically, the storage layer 190 has ears 102 in the first waist region 56a and a substantially rectangular shape in the crotch region 57a and the second waist region 58a. The acquisition/distribution layer 150 is irregularly shaped, being substantially rectangular but having a greater width in the absorbent core crotch region 57a than at the ends 154.

As shown in FIG. 2, acquisition/distribution layer 150 has side edges 152 and end edges 154, tissue layer 170 has side edges 172 and end edges 174, and storage layer 190 has side edges 192 and end edges 194, the foregoing side edges and end edges forming the periphery of the respective layer. The width of acquisition/distribution layer 150 (lateral distance between the side edges 152) in the absorbent core crotch region 57a is slightly greater than the width at the end edges 154 (the acquisition/distribution layer 150 can be rectangular, however, since the waist regions typically do not require absorption characteristics to the extent of the crotch region, cost savings can be achieved by using less material in the waist regions). The lateral distance between the side edges 192 in the region of the ears 102 is greater than the lateral distance between the remaining portion of the side edges 192 of the storage layer 190. This configuration allows wider elasticized side panels 30 in the second waist region 58 (neither shown in FIG. 2).

In FIG. 2, the side edges 152 of acquisition/distribution layer 150 are inside the side edges 192 of the storage layer 190, which side edges 192 are inside the side edges 172 of tissue layer 170. As shown, the acquisition/distribution layer 150 has a smaller surface area than storage layer 190, which in turn has a smaller surface area than tissue layer 170. Preferably, there is a margin from the side edges 152 of the acquisition/distribution layer to the side edges 192 of the storage layer of at least about 0.5 cm in the regions proximate to where fluid is discharged during use. In diapers, this would generally correspond, for example, to the absorbent core crotch region 57a of FIG. 2, particularly at the narrowest part of the storage layer 190 in the absorbent core crotch region 57a. Additionally, especially for absorbent articles to be worn by males, such a margin is maintained in the area to be worn on the front of the wearer, typically the absorbent core first waist region 56a.

FIG. 2 also shows a primary core integrity layer 120 and a secondary core integrity layer 140. The primary core integrity layer is positioned between the backsheet 26 and the storage layer 190. The secondary core integrity layer 140 is positioned between the acquisition/distribution layer 150 and the tissue layer 170. As shown in FIG. 2, the primary core integrity layer 120 is rectangular shaped and has side edges 122 and end edges 124 which form the periphery of primary core integrity layer 120. The secondary core integrity layer 140 is rectangular-shaped, having side edges 142 and end edges 144 which form the periphery of the secondary core integrity layer.

As shown in FIG. 2, secondary core integrity layer 140, storage layer 190, and acquisition/distribution layer 150 are of the same (longitudinal) length, the length of these layers being less than that of topsheet 24, backsheet 26, tissue layer 170, and primary core integrity layer 120, these latter layers being of equal length.

In FIG. 2, the primary core integrity layer 120 envelopes at least a longitudinal portion of the acquisition/distribution layer side edges 152, tissue layer side edges 172 and storage layer side edges 192; and the garment facing surface 100 of the absorbent core 28.

In a preferred embodiment as shown in FIG. 2, the side edges 142 of the secondary core integrity layer 140 will be inside the side edges 152 of the acquisition/distribution layer 150 and inside the side edges 172 of the tissue layer 170.

Figure 3:
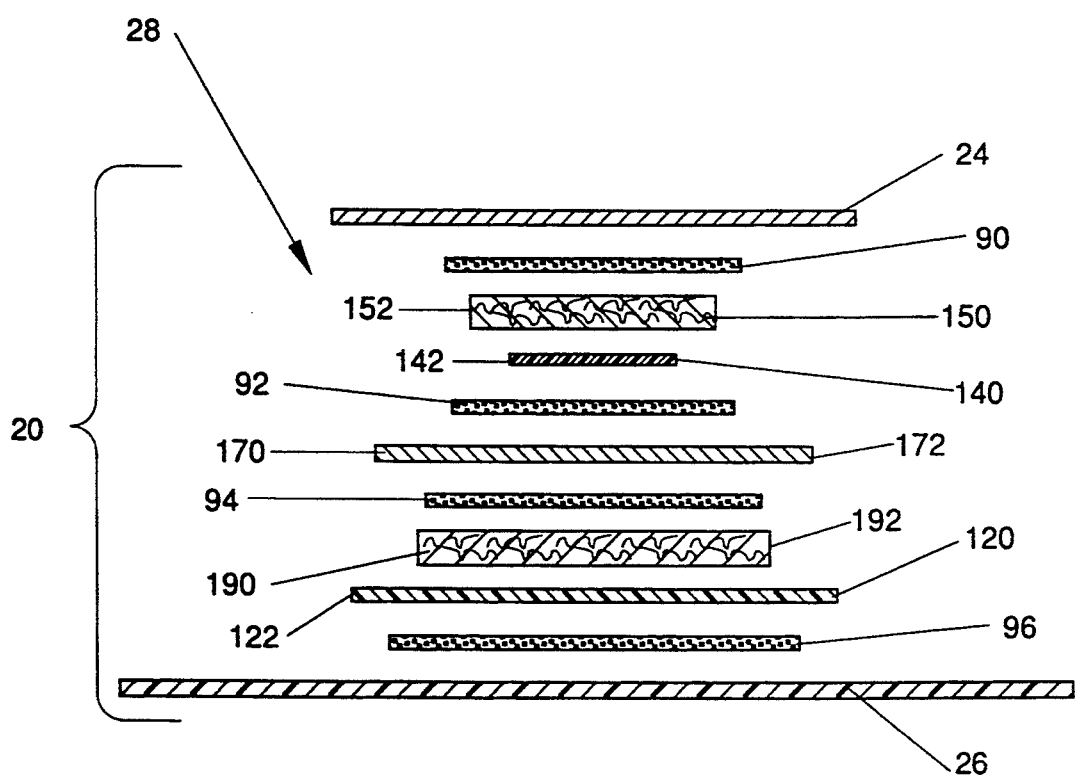
FIG. 3 is a cross-sectional view taken along line 3—3 of FIG. 2.

FIG. 3 is a cross-sectional view of the diaper 20 taken along section line 3—3 of FIG. 2. In addition to showing the core integrity layers 120 and 140 and absorbent core layers 150, 170, and 190 of FIG. 2, FIG. 3 shows construction adhesive layers 90, 92, 94, and 96.

As shown in FIG. 3, the secondary core integrity layer 140 is joined to the tissue layer 170 by construction adhesive layer 92. The secondary core integrity layer 140 is positioned adjacent the acquisition/distribution layer 150. Depending on the bond strength of the secondary core integrity layer 140 material to the acquisition/distribution layer 150, the secondary core integrity layer 140 may be joined to the acquisition/distribution layer 150 by the hot-melt or pressure-sensitive properties of the preferred secondary core integrity layer 140 material. As further shown in FIG. 3, the tissue layer 170 is joined to the storage layer 190 by construction adhesive layer 94. The primary core integrity layer 120 is positioned adjacent the storage layer 190. Depending on the bond strength of the primary core integrity layer 120 material to the storage layer 190, the primary core integrity layer 120 may be joined to the storage layer 190 by the hot-melt or pressure-sensitive properties of the preferred primary core integrity layer 120 material. integrity layer 120 is joined to the backsheet 26 by construction adhesive layer 96, and to the topsheet 24 by the hot-melt or pressure-sensitive properties of the primary core integrity layer 120 material.

As shown in FIG. 3, construction adhesive layer 90 extends outside the side edges 152 of the acquisition/distribution layer 150 and inside the side edges 172 of tissue layer 170. Construction adhesive layer 90 can be wider than the tissue layer 170 so as to effect joinder of the primary core integrity layer 120 to the topsheet 24. However, for economic reasons a separate application of a construction adhesive will usually be made to effect such joinder. Construction adhesive layer 92 is shown in FIG. 3 to extend in the same manner as construction adhesive layer 90. Construction adhesive layer 94 extends inside the side edges 192 of the storage layer 190, and for economic reasons preferably extends a maximum lateral distance of up to about the narrowest width of the storage layer 190 in the absorbent core crotch region 57a. As shown in FIG. 3, construction adhesive layer 96 extends inside the side edges 122 of the primary core integrity layer 120. Construction adhesive layer 96 may alternatively extend outside the side edges 122 of primary core integrity layer 120 in order to effect joinder of backsheet 26 to the topsheet 24. In a preferred embodiment, construction adhesive layers 90, 92, 94, and 96 are applied over the entire length (not shown) of at least one of the acquisition/distribution layer 150, tissue layer 170, storage layer 190, backsheet 26, or topsheet 24.

The backsheet 26 is positioned adjacent the garment surface of the absorbent core 28 and can be joined thereto by attachment means (not shown) such as those well known in the art. (As used herein, the term "joined" encompasses configurations whereby an element is directly secured to the other element by affixing the element directly to the other element (directly joined), and configurations whereby the element is indirectly secured to the other element by affixing the element to intermediate member(s) which in turn are affixed to the other element.) For example, the backsheet 26 may be secured to the absorbent core 28 by a uniform continuous layer of construction adhesive, a patterned layer of construction adhesive, or an array of separate lines, spirals, or spots of construction adhesive. Construction adhesives which have been found to be satisfactory are manufactured by H. B. Fuller Company of St. Paul, Minn. and specified as HL-1258, or those manufactured by Findley Adhesives, Inc. of Wauwatosa, Wis. and designated as H4003 and H2120. The attachment means can comprise an open pattern network of filaments of construction adhesive as is disclosed in U.S. Pat. No. 4,573,986, issued to Minetola et al. on Mar. 4, 1986; or several lines of construction adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. The construction adhesive can be applied by a meltblown process, including a process as described herein for making the primary core integrity layer. The attachment means may alternatively comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is positioned adjacent the body facing surface of the absorbent core 28 and is preferably joined thereto and to the backsheet 26 by attachment means (not shown) such as those well known in the art. Suitable attachment means are described with respect to joining the backsheet 26 to the absorbent core 28.

The topsheet 24 is compliant, soft feeling, and nonirritating to the wearer's skin. Further, the topsheet 24 is liquid pervious, permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 may be made of a hydrophobic material to isolate the wearer's skin from liquids contained in the absorbent core 28. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The absorbent core 28 may be any absorbent means which is generally compressible, conformable, 0 non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, an absorbent gelling material gradient, or lower average density and lower average basis weight acquisition zones; or may comprise one or more layers or structures, i.e., members, including sheets or webs. In addition, each member need not be formed of a single unitary piece of material, but may be formed of a number of smaller strips or components joined together lengthwise or width-wise, as long as they are in fluid communication with one another.) The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,765,780 entitled "Apparatus For and Method of Providing a Multiplicity of Streams of Air-Entrained Fibers" issued to Angstadt on Aug. 23, 1988; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference. In a preferred embodiment, the absorbent core comprises a dusting layer, e.g., as described in the above referenced U.S. Pat. Nos. 4,888,231 and 4,765,780.

The absorbent core preferably comprises absorbent members comprising fibrous webs or batts which comprise both entangled masses of hydrophilic fibers and particles of absorbent gelling material. As used herein, the term "hydrophilic" describes fibers or the surfaces of fibers which are wetted by the liquids deposited onto the fibers. As discussed in detail in The American Chemical Society publication entitled *Contact Angle, Wetability, and Adhesion* edited by Robert F. Gould and copyrighted in 1964, a fiber or surface of a fiber is said to be wetted by a liquid either when the contact angle between the liquid and the fiber or surface is less than 90° or when the liquid will tend to spread spontaneously across the surface of the fiber; both conditions normally coexisting.

Any type of hydrophilic fibrous material which is suitable for use in conventional absorbent products are suitable for use in the absorbent core herein. Specific examples of such hydrophilic fibrous materials include cellulose fibers, modified cellulose fibers, rayon, polyester fibers such as polyethylene terephthalate (DACRON), hydrophilic nylon (HYDROFIL), and the like. Other examples of suitable hydrophilic fibrous materials include hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. For reasons of availability and cost, cellulose fibers, in particular airfelt, are preferred for use in the absorbent core, particularly the storage layer described herein.

Other cellulosic fiber materials which may be especially useful in certain absorbent members herein are the stiffened, twisted, curled, cellulosic fibers which can be produced by internally cross-linking cellulose fibers with a cross-linking agent. Fibers of this general type are disclosed, for example, in Bernardin, U.S. Pat. No. 3,224,926, issued Dec. 21, 1965; Steiger, U.S. Pat. No. 3,241,553, issued Mar. 22, 1966; Chung, U.S. Pat. No. 3,440,135, issued Apr. 22, 1969; Steiger, U.S. Pat. No. 3,658,613, issued Apr. 26, 1972; Chatterjee, U.S. Pat. No. 3,932,209, issued Jan. 13, 1976; and Sangenis et al., U.S. Pat. No. 4,035,147, issued Jul. 12, 1977. Each of these patents is incorporated herein by reference.

One type of stiffened, twisted, curled cellulose fiber which may be useful as the hydrophilic fiber component of the absorbent members herein comprises cellulose fibers which have been internally cross-linked, for example, with a $C_2$–$C_8$ dialdehyde or a $C_2$–$C_9$ polycarboxylic acid crosslinking agent, while such fibers are in a relatively dehydrated state. Such fibers can be defined in terms of their dry fiber and wet fiber twist counts. Fibers of this type and processes of making the same are described in greater detail in European Patent Publication No. 251,676, published Jan. 7, 1988; and in European Patent Publication No. 252,650, published Jan. 13, 1988 (both filed in the name of The Procter & Gamble Company); U.S. Pat. No. 4,822,453, issued Apr. 18, 1989 to Dean et al.; U.S. Pat. No. 4,888,093, issued Dec. 19, 1989 to Dean et al.; U.S. Pat. No. 4,898,642, issued Feb. 6, 1990 to Moore et al.; and U.S. Pat. No. 5,137,537, issued Aug. 11, 1992 to Herron et al. Each of these publications and patents are incorporated herein by reference.

It may be desirable in some applications to include some quantity of hydrophobic fibrous material in the absorbent members, particularly in the acquisition/distribution layer described herein. Such hydrophobic fibrous materials may include, for example, synthetic fibers comprised of rayon, polyethylene, polypropylene, polyethylene terephthalate, or blends thereof. The use of such hydrophobic fibrous materials, as well as hydrophilic and hydrophilized hydrophobic fibrous materials (synthetic or natural), is described in greater detail in U.S. Pat. No. 5,217,445 issued to Young et al. on Jun. 8, 1993; U.S. patent application Ser. No. 07/625,776, filed by Cook et al. on Dec. 17, 1990, and published as International Publication No. WO/91/11163 on Aug. 8, 1991; and U.S. patent application Ser. No. 07/625,774, filed by Lash on Dec. 17, 1990 and published as International Publication No. WO/91/11162 on Aug. 8, 1991; each being incorporated herein by reference.

Other fibrous materials which may be suitable for inclusion in the absorbent core include capillary channel fibers, such as those described in greater detail in European Patent Publication No. 391,814, filed in the name of the Eastman Kodak Company and published Oct. 10, 1990, which publication is incorporated herein by reference.

Such hydrophobic fibers, when used, are preferably present in a comparatively small quantity, typically on the order of about 30% or less (total web weight basis) such that the web remains substantially hydrophilic. The addition of such hydrophobic fibrous materials to the absorbent core may provide improved wicking properties, as well as improved capacity, structural integrity, and resiliency.

In addition to hydrophilic fibrous material, the absorbent member also preferably contains discrete particles of absorbent gelling material. Absorbent gelling materials are those materials which, upon contact with liquids such as water and body fluids, imbibe and retain such liquids and thereby form hydrogels. In this manner, liquids discharged into the absorbent core can be acquired and held by the particles, thereby providing enhanced absorbent capacity and/or improved liquid retention performance.

The particles of absorbent gelling material can be of any desired shape, e.g., spiral or semi-spiral, cubic, rodlike, polyhedral, spherical, etc. Shapes having a large greatest dimension/smallest dimension ratio, such as needles, flakes, and fibers, may also be used herein. Particles also include conglomerates of individual particles. Preferred absorbent gelling materials for use in the present invention are "nonfibrous" particles, i.e., the length to diameter ratio of the particulate material is about 10 or less.

The absorbent gelling material can be an inorganic material such as a silica gel or an organic compound such as a cross-linked polymer. However, the absorbent gelling material will generally comprise a substantially water-insoluble, slightly cross-linked, partially neutralized, hydrogel-forming polymer material. Such absorbent gelling materials can be prepared from polymerizable, unsaturated, acid-containing monomers.

Suitable unsaturated acidic monomers for use in preparing the absorbent gelling materials used in this invention include those listed in U.S. Pat. No. RE 32,649, issued to Brandt et al. on Apr. 19, 1988, which is incorporated herein by reference. Preferred monomers include acrylic acid, methacrylic acid, and 2-acrylamido-2-methyl propane sulfonic acid, with acrylic acid being most preferred. The polymeric component formed from the unsaturated, acid-containing monomers may be grafted onto other types of polymer moieties such as starch or cellulose. Preferred absorbent gelling materials which can be prepared from conventional types of monomers include hydrolyzed acrylonitrile grafted starch, acrylic acid grafted starch, polyacrylates, maleic anhydride copolymers and combinations thereof, with polyacrylates and acrylic acid grafted starch being most preferred.

Whatever the nature of the basic polymer components of the absorbent gelling materials used herein, such materials will in general be slightly cross-linked. Cross-linking serves to render the absorbent gelling materials substantially water-insoluble, and cross-linking thus in part determines the gel volume (and Absorbent Capacity) and extractable polymer characteristics of the hydrogels formed from the absorbent gelling material. Suitable cross-linking agents are well known in the art and include, for example, those described in greater detail in U.S. Pat. No. 4,076,663, issued to Masuda et al. on Feb. 28, 1978, which is incorporated herein by reference. Preferred cross-linking agents are the di- or polyesters of unsaturated mono- or polycarboxylic acids with polyols, the bisacrylamides, and the di- or triallyl amines; with N,N'-methylenebisacrylamide, trimethylol propane triacrylate, and triallyl amine being most preferred. The cross-linking agent will generally comprise from about 0.001 mole percent to 5 mole percent, preferably from about 0.01 mole percent to 3 mole percent, of the resulting absorbent gelling material.

The slightly cross-linked, absorbent gelling materials which may be used in the present invention are generally employed in their partially neutralized form. For purposes of this invention, such materials are considered partially neutralized when at least 25 mole percent, preferably at least 50 mole percent, of monomers used to form the polymer are acid group-containing monomers which have been neutralized with a salt-forming cation such as alkali metal, ammonium, substituted ammonium, and amines. The percentage of the total monomers utilized which are neutralized acid group-containing monomers is referred to herein as the "degree of neutralization" and is preferably not greater than 98%.

The absorbent gelling materials used in the absorbent cores herein preferably have a relatively high capacity for imbibing fluids encountered in absorbent cores of absorbent articles (in the context of the present invention, it should be noted that the term "fluid" means "liquid."). For purposes of this invention, the Absorbent Capacity can be defined in terms of the amount of Synthetic Urine (1.0% NaCl aqueous solution, prepared using distilled water) absorbed by any given absorbent gelling material and is specified as grams of Synthetic Urine per gram of absorbent gelling material. The absorbent cores of the present invention, and especially the ones which are to be used in diapers, adult incontinence products or training pants, will generally employ absorbent gelling material having an Absorbent Capacity of at least about 10 grams (g), preferably at least about 15 grams, more preferably at least about 20 grams, of Synthetic Urine per gram of absorbent gelling material. A method of determining Absorbent Capacity suitable for use herein is described in detail in the above referenced U.S. Pat. No. 5,217,445 issued to Young, et al. on Jun. 8, 1993 as "Superabsorbent Material Absorbent Capacity Test Method."

When the absorbent member is constructed from cellulosic fibers such as wood pulp fibers (airfelt), it may be desirable to utilize absorbent gelling material having a somewhat higher Absorbent Capacity, i.e., an Absorbent Capacity between about 25 and 60 grams of Synthetic Urine per gram of absorbent gelling material. On the other hand, absorbent members constructed from the stiffened, twisted, curled cellulosic fibers hereinbefore described may actually be more effective at absorbing fluid if absorbent gelling materials of somewhat lower Absorbent Capacities are employed, for example, from about 20 to 35 grams of Synthetic Urine per gram of absorbent gelling material. These applications are described in more detail in U.S. patent application Ser. No. 08/042,950, filed by Payne et al. on Apr. 5, 1993, which is incorporated herein by reference.

Another feature of the absorbent gelling materials relates to the level of extractable polymer material present in the absorbent gelling material. Extractable polymer levels are defined and can be determined as described in the above referenced U.S. Pat. No. RE 32,649. Preferred absorbent gelling materials have an equilibrium extractables content in Synthetic Urine of no more than about 17%, preferably no more than about 10%, by weight of the absorbent gelling material Absorbent gelling materials having high gel strength are particularly useful herein. Gel strength refers to the tendency of the particles of absorbent gelling material to deform or spread under stress once the particles absorb liquids (gel deformation tendency). The gel strength should be such that the particles of absorbent gelling material do not deform and fill to an unacceptable degree the capillary void space in the absorbent core, thereby inhibiting both absorbent capacity of the absorbent core and fluid distribution throughout the absorbent core. For a given type of absorbent gelling material, gel strength will generally decrease as the gel volume (and Absorbent Capacity) increases. It has been found that it is desirable to utilize an absorbent gelling material which has as high a gel strength as possible consistent with the realization of an acceptably high Absorbent Capacity.

Gel strength can be specified in terms of the shear modulus of the particles of absorbent gelling material. Shear modulus can be measured using a procedure described in greater detail in the above referenced U.S. Pat. No. RE 32,649. Absorbent gelling materials which have been found to be particularly useful in the present invention exhibit a shear modulus of at least about 2,000 dynes/$cm^2$, more preferably, about 2,500 to about 92,000 dynes/$cm^2$ and most preferably of from about 5,000 to about 35,000 dynes/$cm^2$.

The absorbent gelling material particles may have a particle size varying over a wide range. However, various considerations may preclude the use of very small or very large particles. For reasons of industrial hygiene, average particle sizes smaller than about 30 microns are less desirable. Particles having a smallest dimension larger than about 2 millimeters may cause a feeling of grittiness in the absorbent core, which is undesirable from a consumer aesthetics standpoint. Furthermore, the rate of fluid absorption is affected by particle size. Larger particles tend to have very much reduced absorption rates. The absorbent gelling material particles for use herein will typically have an average particle size of from about 50 microns to about 1000 microns.

In certain embodiments of the present invention, it may be desirable to use absorbent gelling materials in the form of nonfibrous particles having a relatively large particle size and other particle size characteristics. Improved absorbent capacity, acquisition, and distribution within the absorbent core may be realized by incorporating such particles. Specifically, the absorbent core can include absorbent gelling material particles of a selected mass median particle size and a certain particle size deviation from the mass median particle size as determined by sieve size analysis. The use of these relatively large particle size absorbent gelling materials is described in detail in the above referenced U.S. patent application Ser. No. 08/042,950 (Payne et al.).

Absorbent gelling material particles having relatively large particle size ranges include interparticle cross-linked aggregates. Such aggregate particles are formed by joining together two or more previously independent precursor particles of the types set forth above by interparticle cross-linking agents applied thereto and subjected to conditions, while maintaining the physical association of the precursor particles, which are sufficient to react the interparticle cross-linking agent with the polymer material of the precursor particles to form cross-link bonds between the precursor particles that form the aggregate. Such aggregates, as well as methods of forming them, are described in greater detail in U.S. Pat. No. 5,149,334, issued Sep. 22, 1992 to Lahrman et al., which is incorporated herein by reference.

Relatively large particle size absorbent gelling materials can also be prepared by agglomeration of smaller particles to produce larger agglomerates. Agglomeration techniques are well known in the art and may involve the use of moisture addition to smaller particles or the use of a binder or other type of agglomerating medium.

As noted, the particles of absorbent gelling material can be in fibrous form. Fibrous absorbent gelling materials have been previously disclosed in the art. For example, fibrous absorbent gelling materials are described in *Textile Science and Technology*, Volume 7, Pronoy K. Chatterjee, editor, Elsevier Science Publishers B.V. (The Netherlands), 1985, in Chapters VII and VIII (collectively pages 217–280), incorporated by reference herein. Synthetic and modified natural fibers, such as cellulosic fibers, can be used. One type of absorbent gelling material fiber comprises the polycarboxylate polymer-modified cellulosic fibrous pulps such as mildly hydrolyzed methyl acrylate-grafted softwood kraft pulps. These absorbent gelling material fibers are described in U.S. Pat. No. 4,986,882, issued on Jan. 22, 1991 to Mackey, et al.; which is incorporated herein by reference. Other types of fibrous absorbent gelling material include crosslinked carboxymethyl cellulose and polymer grafted cellulose fibers including hydrolyzed polyacrylonitrile, polyacrylic ester, and polyacrylic and polymethacrylic acid grafted cellulose fibers. A discussion of these materials and processes for making them can be found in Chatterjee's Vol. 7 of *Textile Science and Technology*, which references "Radiation Grafting of Acrylic and Methacrylic Acid to Cellulose Fibers to Impart High Water Sorbency," A. H. Zahran, et al., J. of App. Polymer Science, Vol. 25, 535–542 (1980); U.S. Pat. No. 4,036,588, Williams, et al., issued Jul. 19, 1977; and U.S. Pat. No. 3,838,077, Hoftiezer, et al., issued Sep. 24, 1974. Each of these references is incorporated herein by reference.

The relative amount of hydrophilic fibrous material and absorbent gelling material particles used in the absorbent members of the present invention can be most conveniently expressed in terms of a weight percentage of the absorbent member. In order to minimize the thickness of the absorbent article, it may be desired to maximize the concentration of absorbent gelling material in certain absorbent members, particularly an absorbent member to be used for fluid storage such as the storage layer described herein. Thus, the absorbent member may contain from about 2% to about 90% preferably from about 30% to about 85%, more preferably about 30% to about 70%, most preferably from about 40% to about 70%, by weight of the absorbent member, of absorbent gelling material. This concentration of absorbent gelling material can also be expressed in terms of a weight ratio of hydrophilic fiber to particulate absorbent gelling material, the ratios ranging from about 10:90 to about 98:2.

In addition, the particles of absorbent gelling material may be dispersed in various weight ratios throughout different regions and thicknesses of the absorbent member.

In an alternative embodiment of the present invention, the absorbent member comprises an absorbent foam. Absorbent foams which are particularly useful for use in the absorbent members of the present invention are the hydrophilic, open-celled foams disclosed in U.S. patent application Ser. No. 07/743,839, filed on Aug. 12, 1991 by DesMarais et al., and published as International Publication No. 93/04092; and U.S. patent application Ser. No. 08/989,270, filed on Dec. 11, 1992 by Dyer, et al. Other absorbent foams which are suitable for use herein are described in U.S. patent application Ser. Nos. 08/038,580 and 08/037,803, both filed on Mar. 26, 1993 in the name of Phan et al. Each of these Patent Applications and the International Publication are incorporated herein by reference.

In another embodiment of the present invention, the absorbent member comprises a sheet material comprised of absorbent gelling material. Such sheet materials which are particularly useful in the absorbent members of the present invention include absorbent polymeric macrostructures that are porous and which comprise an interparticle cross-linked aggregate. Such macrostructures are described in detail in U.S. Pat. No. 5,102,597, issued to Roe et al. on Apr. 7, 1992; and U.S. Pat. No. 5,124,188, issued to Roe et al. on Jun. 23, 1992; each patent being incorporated herein by reference. Other sheet materials comprising interparticle cross-linked aggregates which are suitable for use in the absorbent cores of the present invention are described in U.S. patent application Ser. No. 07/684,712, filed on Apr. 12, 1991 by Kolodesh et al.; and U.S. patent application Ser. No. 07/955,635, filed on Oct. 10, 1992 by Rezai et al. Each of these patent applications are incorporated herein by reference.

In a preferred embodiment as is shown in FIG. 2, the absorbent core a 28 has fluid acquisition/distribution layer and a fluid storage layer (hereinafter alternatively referred to as acquisition/distribution layer and storage layer, respectively). The acquisition/distribution layer is typically positioned relative to the storage layer such that the absorbent core comprises an upper acquisition/distribution layer and a lower storage layer. For purposes of this invention, the term "upper" refers to the layer of the absorbent core which is nearest to and faces the absorbent article topsheet; conversely, the term "lower" refers to the layer of the absorbent core which is nearest to and faces the absorbent article backsheet (similarly, "upper surface" and "lower surface" refer to the surface of a layer which is nearest to and faces the absorbent article topsheet or backsheet, respectively). An upper fluid acquisition/distribution layer 150 and a lower fluid storage layer 190 are shown in FIGS. 2 and 3. For purposes of the present invention, the upper acquisition/distribution layer and the lower storage layer refer merely to the upper and lower zones of the absorbent core and are not necessarily limited to single layers or sheets of material. As used herein, the term "layer" includes the terms "layers" and "layered." Thus, both the fluid acquisition/distribution layer and the fluid storage layer may actually comprise laminates or combinations of several sheets or webs of the requisite type of materials as hereinafter described.

Cores comprising an upper acquisition/distribution layer and a lower storage layer suitable for use herein are described in the above referenced and incorporated U.S. Pat. Nos. 4,673,402 (Weisman et al.) and 5,217,445 (Young et al.); International Publication Nos. WO/91/11162 (Lash) and WO/91/11163 (Cook et al.); and U.S. patent application Ser. No. 08/042,950 (Payne et al.).

The fluid acquisition/distribution layer serves to quickly collect and temporarily hold discharged body fluid. A portion of discharged fluid may, depending upon the wearer's position, permeate the acquisition/distribution layer and be absorbed by the storage layer in the area proximate to the discharge. However, since fluid is typically discharged in gushes, the storage layer in such area may not absorb the fluid as quickly as it is discharged. Therefore, the acquisition/distribution layer hereof also facilitates transport of the fluid from the point of initial fluid contact to other parts of the acquisition/distribution layer.

The acquisition/distribution layer comprises hydrophilic fibrous material as described herein, and is preferably a web comprising chemically stiffened cellulosic fibers. The preferred acquisition/distribution layer comprises from about 50% to 100% of these fibers and from 0% to about 50% of a binding means.

The fluid distribution function of the acquisition/distribution layer is of particular importance in order to more fully utilize the capacity of the storage layer. The presence of substantial amounts of absorbent gelling material in the acquisition/distribution layer which swell upon contact with fluids is believed to adversely affect this function of the acquisition/distribution layer. A variety of other factors relating to the fluid acquisition/distribution layer of the absorbent structures herein can be of importance in determining the effectiveness of the resulting absorbent articles. These include shape, basis weight, density, permeability, capillarity and wicking ability, the type and structural integrity, and character of the fibrous material utilized.

The acquisition/distribution layer in the unfolded configuration can be of any desired shape, for example, rectangular, trapezoidal, oval, oblong, hourglass, or irregularly-shaped. The shape of the fluid acquisition/distribution layer of the absorbent core can, but need not necessarily, correspond to the general shape of the storage layer. The acquisition/distribution layer of the core is preferably elongated. For purposes of this invention, this means that the acquisition/distribution layer, like the storage layer, is elongated if it is of unequal length and width in the unfolded, flat configuration.

The top surface area of the acquisition/distribution layer will preferably range from about 25% to about 90% of the top surface area of the storage layer, and also preferably will not extend beyond the edge of the storage layer at any outer boundary. The acquisition/distribution layer will typically have a top surface area of less than about 80% of that of the storage layer.

The fluid acquisition/distribution layer will generally have an average dry density of less than about 0.30 g/cm$^3$ measured prior to use, and an average density upon wetting to saturation with Synthetic Urine (1.0% NaCl aqueous solution, prepared with distilled water), on a dry weight basis, of less than about 0.20 g/cm$^3$, preferably less than about 0.15 g/cm$^3$. Preferably, the average dry density and density upon wetting to saturation are between about 0.02 g/cm$^3$ and 0.20 g/cm$^3$, more preferably between about 0.02 g/cm$^3$ and about 0.15 g/cm$^3$. The average dry basis weight of the acquisition/distribution layer will typically range from about 0.001 to about 0.10 g/cm$^2$, preferably from about 0.01 to about 0.08 g/cm$^2$, more preferably from about 0.015 to about 0.04 g/cm$^2$. Density and basis weight can be substantially uniform although nonuniform density and/or basis weight, and density and/or basis weight gradients, are meant to be encompassed herein. Thus, the acquisition/distribution layer can contain regions of relatively higher or relatively lower density and basis weight, preferably not exceeding the foregoing ranges. Densities and basis weights can be determined as described in the above referenced International Publication No. WO/91/11163. Density and basis weight values include the weight of any absorbent gelling material.

As stated, the acquisition/distribution layer preferably comprises a web of hydrophilic, chemically stiffened cellulosic fibers. Such webs comprising chemically stiffened cellulosic fibers are described in detail in the above referenced and incorporated International Publication No. WO/91/11163.

The stiffened fibers include those described in the above referenced and incorporated U.S. Pat. Nos. 3,224,926 (Bernardin); 3,440,135 (Chung); 3,932,209 (Chatterjee) and 4,035,147 (Sangenis et al.). More preferred fibers are disclosed in the above referenced and incorporated U.S. Pat. Nos. 4,822,453 (Dean et al.); 4,888,093 (Dean et al.); 4,898,642 (Moore et al.); and 5,137,537 (Herron et al.); and European Patent Publication Nos. 251,676 and 252,650.

In the presently most preferred embodiment, a $C_2$-$C_9$ polycarboxylic acid stiffening agent, more preferably citric acid, is used. Fibers crosslinked with such agents and a method of preparing the same is described in U.S. Pat. No. 5,137,537. These fibers preferably have an average dry fiber twist count of at least about 2.5 twist nodes per millimeter (mm), and an average wet fiber twist count of at least about 1.5 twist nodes per mm and which is at least 1.0 twist nodes per mm less than its dry fiber twist count. Most preferably, the average dry fiber twist count is at least about 3.0 twist nodes per mm, and the average wet fiber twist count is at least about 2.0 twist nodes per mm and which is at least 1.0 twist nodes per mm less than the dry fiber twist count. These fibers also preferably have a curl factor of at least about 0.30, more preferably at least about 0.50. In addition, the water retention value (WRV) is preferably less than about 60%, more preferably between about 28% and about 50%, most preferably from about 30% to 45%. Twist counts, curl factor, and WRV are defined in U.S. Pat. No. 5,137,537 and can be determined as described therein.

The stiffened cellulosic fibers can be provided in web form by various techniques, including airlaying and wetlaying. Suitable methods of forming airlaid and wetlaid webs are disclosed in the above referenced and incorporated International Publication Nos. WO/91/11162 and WO/91/11163; and in U.S. Pat. Nos. 5,217,445 and 5,137,537. Suitable wetlaying techniques are also disclosed in U.S. Pat. No. 3,301,746, issued to Sanford, et al.; and U.S. Pat. No. 4,889,597, issued Dec. 26, 1989; both incorporated herein by reference.

The fluid acquisition/distribution layer preferably contains no more than about 6.0% of absorbent gelling material. More preferably, the acquisition/distribution layer will be substantially free of absorbent gelling material. For purposes herein, "substantially free" of absorbent gelling material means less than about 2.0%, preferably less than about 1.0%, more preferably zero or essentially zero percent absorbent gelling material. As used herein, "essentially zero" percent absorbent gelling material means low amounts (less than about 0.5%) of absorbent gelling material present in the acquisition/distribution layer incidental to the contact or close proximity of the absorbent gelling material-containing storage layer with the acquisition/distribution layer.

The fluid storage layer of the preferred absorbent core comprises hydrophilic fiber and absorbent gelling material, such as the fibers and materials previously described. The principal function of the fluid storage layer is to absorb discharged body fluid from the acquisition/distribution layer and retain such fluid under the pressures encountered as a result of the wearer's movements. Thus, the storage layer is typically subjacent to (i.e., is a lower storage layer) and in fluid communication with the acquisition/distribution layer. Ideally the fluid storage layer will drain the acquisition/distribution layer of much of its acquired fluid load. Fluids such as body fluids which are discharged into the acquisition/distribution layer and transported to the storage layer can be acquired and held by the absorbent gelling material, thereby providing the articles herein with enhanced absorbent capacity and/or improved fluid retention performance.

The absorbent gelling material in the storage layer will most often comprise a substantially water-insoluble, slightly cross-linked, partially neutralized, polymeric absorbent gelling material as previously described. The absorbent gelling material can be in any form which can be incorporated into a flexible web or sheet to form the storage layer and will typically be in the form of discrete particles as previously described. These particles will typically be distributed within a web of fibrous material (as previously described) as carrier means. Preferred fibrous carrier means are cellulose fibers, in the form of fluff (airfelt), such as is conventionally utilized in absorbent cores. Modified cellulose fibers such as the stiffened cellulose fibers described herein can also be used, but are preferably not used, in the storage layer.

In order to minimize the thickness of the absorbent article, it may be desired to maximize the amount of absorbent gelling material in the storage layer, consistent with obtaining desired fluid handling properties. For example, the storage layer may comprise from 2% to about 90% absorbent gelling material, and from about 98% to about 10% of a fibrous carrier means which comprises hydrophilic fiber. The presently preferred storage layers comprise from about 30% to about 85%, more preferably from about 30% to about 70%, most preferably from about 40% to about 70%, of absorbent gelling material; and from about 70% to about 15%, more preferably from about 70% to about 30%, most preferably about 60% to about 30%, of the carrier means.

The absorbent gelling material can be uniformly distributed in the storage layer. Alternatively, there may be regions or zones of the storage layer which have higher concentrations of absorbent gelling material than do other regions or zones of the layer (i.e., a gradient). For example, more absorbent gelling material may be present in regions of relatively high fluid handling requirements (e.g., near the region of fluid discharge) and less absorbent gelling material at lower demand regions.

The average dry density of the fluid storage layer comprising non-absorbent gelling material fibers as absorbent gelling material carrier means will generally be in the range of from about 0.06 to about 0.5 g/cm$^3$, preferably within the range of from about 0.10 to about 0.4 g/cm$^3$, more preferably from about 0.15 to about 0.3 g/cm$^3$, most preferably from about 0.15 to about 0.25 g/cm$^3$. Typically the basis weight of the fluid storage layer can range from about 0.02 to 0.12 g/cm$^2$, preferably from about 0.04 to 0.08 g/cm$^2$, most preferably from about 0.05 to 0.07 g/cm$^2$. As with the acquisition/distribution layer, density and basis weight need not be uniform throughout the storage layer. The storage layer can contain regions of relatively higher and relatively lower density and basis weight. Basis weight and density values are determined in the same manner as for the acquisition/distribution layer.

The storage layer embodiments of the absorbent core comprising the fibrous carrier means can be formed by air-laying a substantially dry mixture of fibers and absorbent gelling material particles and, if desired or necessary, densifying the resulting web. Such a procedure is in general described more fully in the hereinbefore referenced U.S. Pat. No. 4,610,678 issued to Weisman et al. on Sep. 9, 1986.

It is also contemplated to provide a storage layer wherein particles of absorbent gelling material are laminated between two or more webs of fibrous material, such as exemplified in U.S. Pat. No. 4,578,068, Kramer et al., issued Mar. 25, 1986, incorporated herein by reference.

The storage layer may also comprise fibrous absorbent gelling material. Absorbent gelling material fibers can be combined with fibrous, non-absorbent gelling material carrier means according to conventional airlaid or wetlaid web-forming processes. Absorbent gelling material fibers can also be formed into nonwoven sheets, which may consist essentially of fibrous absorbent gelling material with substantially zero percent carrier means, or which may include carrier means. Nonwoven sheets made from fibrous absorbent gelling material such as the non-acrylate absorbent gelling material microfibers are available from Arco Chemical Co. (Newtown Square, Pa., USA), under the tradename FIBERSORB TM, and from Japan Exlan Co., Ltd. (Osaka, Japan) which markets absorbent gelling material fibers comprising a polyacrylonitrile core with a polyacrylic acid/polyammonium acrylate skin under the tradename LANSEAL TM.

The storage layer can alternatively comprise a single sheet of essentially 100% absorbent gelling material, for example, the polymeric macrostructures comprising interparticle cross-linked aggregates described in the above-referenced and incorporated U.S. Pat. Nos. 5,102,597 and 5,124,188; and U.S. patent application Ser. Nos. 07/684,712 and 07/955,635. The storage layer can also comprise a single sheet of hydrophilic foam such as those described in the above referenced and incorporated U.S. patent application Ser. Nos. 07/743,839; 08/989,270; 08/038,580; and 08/037,803.

The acquisition/distribution layer of the absorbent core can have a surface area (in an unfolded configuration) which is less than, equal to, or greater than that of the storage layer. In the present invention, the acquisition/distribution layer preferably has a smaller surface area than that of the storage layer and, in fact, can have a surface area that is substantially smaller than that of the fluid storage layer. Generally, the surface area of the acquisition/distribution layer will range from about 25% to about 100%, preferably from about 30% to about 95%, more preferably less than about 90%, most preferably less than about 85%, of the surface area of the storage layer.

In accordance with the present invention, the acquisition/distribution layer of the absorbent core should be placed in a specific positional relationship with respect to the topsheet and the storage layer of the absorbent article. More particularly, the acquisition/distribution layer of the absorbent core must be positioned so that it is effectively located to acquire discharged body fluid and transport said fluid to other regions of the absorbent core. Thus, the acquisition/distribution layer should encompass the vicinity of the point of discharge of body fluids. These areas would include the crotch area and, preferably for males, also the region where urination discharges occur in the front of the diaper. For a diaper, the front of the absorbent articles herein means the portion of the absorbent article which is intended to be placed on the front of the wearer. Additionally, for males, it is desirable for the acquisition/distribution layer to extend to near the front waist area of the wearer to effectively acquire the relatively high fluid load that occurs in the front of the male wearer, and to compensate for directional variations of the discharges. The corresponding absorbent article regions will vary depending upon the design and fit of the absorbent article. FIG. 2 exemplifies one embodiment wherein the acquisition/distribution layer 150 is suitably positioned to receive both bowel and urine discharges for both males and females.

For disposable baby diaper executions, the acquisition/distribution layer of the absorbent core is preferably positioned relative to the elongated topsheet and/or the storage layer such that the acquisition/distribution layer is sufficiently elongated to extend to areas corresponding at least to about 50%, preferably 75%, of the length of the storage layer. The acquisition/distribution layer preferably has a width sufficient to acquire gushes of body fluids without direct discharge of fluid onto the storage layer. Generally, for diapers, such as shown in FIG. 2, the width will be at least about 5 cm, preferably at least about 6 cm. For purposes of the present invention, sections of the absorbent article can be defined by reference to top surface areas of the unfolded absorbent article found in front of a given point on the line which defines the length of the absorbent article (e.g., along the longitudinal centerline 67).

For purposes of determining such acquisition/distribution layer positioning, the length of the absorbent article will be taken as the normal longest longitudinal dimension of the elongated article backsheet. This normal longest dimension of the elongated backsheet can be defined with respect to the article as it is applied to the wearer. When worn, the opposing ends of the backsheet are fastened together so that these joined ends form a circle around the wearer's waist. The normal length of the backsheet will thus be the length of the line running through the backsheet from: (a) the point on the edge of the backsheet at the middle of the wearer's back waist, through the crotch, to (b) the point on the opposite edge of the backsheet at the middle of the wearer's front waist. The length of the topsheet will generally correspond substantially to that of the backsheet.

In the usual instance wherein the storage layer of the absorbent core generally defines the shape of the absorbent article, the normal length of the elongated article topsheet will be approached by the longest longitudinal dimension of the storage layer of the core. However, in some applications (e.g., adult incontinence articles) wherein bulk reduction or minimum cost are important, the storage layer would not take on the general shape of the diaper or incontinence structure. Rather the storage layer would be generally located to cover only the genital region of the wearer and a reasonable area proximate to the genital area. In this instance both the fluid acquisition/distribution layer and the storage layer would be located toward the front of the article as defined by the topsheet such that the acquisition/distribution and storage layers would typically be found in the front two-thirds of the article.

The storage layer and acquisition/distribution layer of the absorbent core can be of any desired shape consistent with comfortable fit and/or the sizing limitations discussed herein, including, for example, circular, rectangular, trapezoidal, oblong, hourglass-shaped, dog-bone-shaped, half dog bone shaped, oval or irregularly shaped. The acquisition/distribution layer can be of similar shape or differing shape than the storage layer. The storage layer need not be physically separated from the acquisition/distribution layer and can simply be a zone of absorbent gelling material concentration in a continuous web of stiffened cellulose fiber material. More preferably, however, the storage layer of the absorbent core will comprise a separate web which can be used as an insert placed underneath the acquisition/distribution layer, such as shown in FIG. 3.

In yet another preferred embodiment, a fluid pervious sheet (e.g., a paper tissue sheet or other scrim) positioned between the acquisition/distribution layer and the storage layer to increase integrity of the acquisition/distribution layer during processing and/or use. Such a fluid impervious sheet is shown in FIGS. 2 and 3 as tissue layer 170. The fluid pervious sheet can envelope all or part of the acquisition/distribution layer (as shown in FIGS. 2 and 3), or simply be positioned as described above without necessarily enveloping the acquisition/distribution layer. Also, optionally, the storage layer can be enveloped with a fluid pervious sheet, such as a paper tissue sheet, to obviate user concerns with loose absorbent gelling material which may be incorporated into the storage layer.

The diaper 20 comprises a primary core integrity layer which preferably envelopes at least one layer of the absorbent core 28 and which is joined, preferably directly joined, to a chassis component (e.g., the topsheet 24 or backsheet 26) of the diaper 20. The primary core integrity layer tends to improve the integrity of the absorbent layers which it envelopes. Thus, in a preferred embodiment, the primary core integrity layer envelopes each of the layers of the absorbent core 28. The following description is therefore directed to a primary core integrity layer which envelopes each of the layers of the absorbent core 28. It should be understood, however, that improvements in absorbent core integrity may be obtained by using a configuration in which the primary core integrity layer envelopes only one or some of the absorbent layers of the absorbent core 28. For example, the integrity of an acquisition/distribution layer described herein, and thus of the absorbent core incorporating the same, can be improved by enveloping only the acquisition/distribution layer with a primary core integrity layer. In addition, a primary core integrity layer which does not envelope any of the absorbent core layers can be used to improve the absorbent core integrity. This embodiment is also encompassed by the present invention. For example, the surface area dimensions of the primary core integrity layer can be less than those of each absorbent core layer (the primary core integrity layer would then be positioned and joined as described herein for a secondary core integrity layer which does not envelope any of the absorbent core layers). However, it is believed that enhanced absorbent core integrity is achieved where the primary core integrity layer envelopes at least one absorbent core layer, such that this embodiment is preferred.

By "enveloped," it is meant that the primary core integrity layer encloses or surrounds at least a portion of the absorbent core (or layer thereof). In a preferred embodiment, the primary core integrity layer envelopes at least a portion of the absorbent core side edges 82 and at least one of the surfaces 100 or 101 of the absorbent core. The primary core integrity layer will typically envelope the side edges of one or more layers in the y- and z- directions (as used herein, the x- and y-directions correspond to the direction of the lateral center line 66 and the longitudinal center line 67, respectively; the z-direction is normal to the resultant x-y plane). In a preferred embodiment as shown in FIG. 2, the primary core integrity layer 120 envelopes at least a portion of the side edges 152, 172, and 192, and the garment facing surface 100. More preferably, the primary core integrity layer envelopes at least the portion of the side edges 152, 172, and 192 positioned in the absorbent core crotch region 57a. As shown in FIG. 2, the primary core integrity layer 120 envelopes the side edges 152 and 172, and side edges 192 exclusive of the side edge portions 192a lying in the absorbent core ears 102.

The primary core integrity layer tends to provide structural support to the absorbent core. Without intending to be bound by theory, it is believed that the higher elasticity and/or flexibility of the material making up the primary core integrity layer relative to those properties of the fibrous materials of the absorbent core tend to allow the absorbent core to withstand the various forces encountered during use of an absorbent article (e.g., flexural and torsional forces). It is thus believed that the composite, primary core integrity layer-absorbent core structure has increased flexibility and/or elasticity. As a result, the absorbent core has a reduced tendency to break, for example, during use or after being subjected to the forces typically used in packaging disposable absorbent articles. Thus, the absorption by the absorbent core is not limited by breakage gaps which may otherwise occur in the absorbent core such that the entire absorbent core tends to be available for fluid absorption.

The primary core integrity layer additionally serves to hold the absorbent core in a relatively stable position, since the absorbent core will be physically constrained by the primary core integrity layer. It is also believed that the primary core integrity layer helps to maintain the adhesive bonds which typically join the absorbent core and chassis component of absorbent articles, e.g., where a construction adhesive is used to join these components. The primary core integrity layer is particularly useful in maintaining the integrity of the adhesive bonds typically joining cellulosic fibers of the absorbent core to a polymeric chassis, more particularly a chassis formed of or coated with a synthetic polymeric material (hereinafter "synthetic polymeric chassis").

Without intending to be bound by theory, it is believed that the thermoplastic material from which the primary core integrity layer is made forms a bond to a synthetic polymeric chassis component (whether directly joined to the chassis component by its own adhesive properties or by a construction adhesive) having a greater strength than the cellulosic fiber-construction adhesive-polymeric chassis bonds. This is because the primary core integrity layer-polymeric chassis bond (alternatively the primary core integrity layer-construction adhesive-polymeric chassis bond, as will be understood by those of ordinary skill in the art) tends to be relatively cohesive, as compared to the cellulosic fiber-construction adhesive-polymeric chassis bond. It is believed that the more similar the chemistry of the materials being joined, the greater the bond strength. The synthetic polymeric chassis, thermoplastic primary core integrity layer, and construction adhesives are relatively similar in chemistry as compared to the cellulosic fibers. Thus, the former materials can be directly joined to form a relatively strong bond, as compared to the cellulosic fiber-construction adhesive-polymer chassis bond.

Since the primary core integrity layer forms a relatively strong bond and physically constrains the absorbent core, the primary core integrity layer tends to reduce the forces encountered by the relatively weak, cellulosic fiber-construction adhesive-polymeric chassis bonds such that these latter bonds have a reduced tendency toward breakage. Further, if the cellulosic fiber-construction adhesive-polymeric chassis bonds do fail, the relatively strong primary core integrity layer-chassis bond tends to retain the absorbent core in a relatively stable position. Thus, the absorbent core has a reduced tendency to separate from the chassis component. This positive effect on adhesion may be particularly important when the absorbent article is wetted. When the cellulosic fibers and absorbent gelling material which are typically incorporated into the absorbent core expand upon wetting, the forces exerted by the expanding cellulosic fibers and absorbent gelling material tend to cause a loss of adhesion between the fibers, absorbent gelling material, and chassis (adhesive failure tends to occur between the fibers and/or absorbent gelling material and the construction adhesive, rather than the chassis and construction adhesive).

By effectively constraining the absorbent core, the primary core integrity layer also reduces the tendency of absorbent core layers to slip away and/or separate from one another. This tendency toward slippage and/or separation is further reduced where the primary core integrity layer comprises a tacky, pressure-sensitive material. It is believed that the above described physical constraint, relatively strong primary core integrity layer-chassis bond, and/or tack reduce the tendency of the absorbent core or components thereof to slump, break, and/or rope. As a result, the absorbent core is more effectively utilized such that the absorbent article has improved absorption characteristics and reduced leakage.

The primary core integrity layer provides the above improvements without interfering substantially with fluid transport into and through the absorbent core and without requiring a great amount of material.

The primary core integrity layer comprises a continuous, liquid pervious mesh of thermoplastic material. The thermoplastic material is preferably a hot-melt adhesive, more preferably a hot-melt, pressure-sensitive adhesive. The thermoplastic material is also preferably elastomeric.

By "mesh", it is meant that the thermoplastic material is in the form of strands which are interconnected to form apertures. As formed by a meltblown process, the individual strands are preferably sinuous (wavy) and oriented in substantially the same direction with at least some crosswise linking to form an intertwining web of the strands. "Strands" is meant to include fibers, threads, filaments, and other forms which have a relatively large longitudinal to cross-sectional dimension. By "liquid pervious mesh," it is meant that the mesh has a sufficient number of apertures of sufficient size per unit area to allow relatively unimpeded fluid transport through the mesh. Thus, the mesh typically has a basis weight as described herein.

By "continuous" mesh, it is meant that substantially all of the strands are connected to at least one other strand. Typically, the strands are cohesively connected at each of the points where the strands intertwine. (As understood in the art, cohesion refers to the force that holds adjacent molecules of a single material together. As used herein, "relatively cohesive" bonding is believed to result from the force of attraction between two or more similar materials, e.g., two or more synthetic polymeric materials.)

Various thermoplastic materials such as are known in the art may be used for making the primary core integrity layer. A "thermoplastic" material, as that term is used and understood by those skilled in the art, includes any natural or synthetic thermoplastic polymer or polymeric composition. A thermoplastic material is normally a solid or semi-solid material at use temperatures (typically room temperature, i.e., about 20° C. to about 25° C.) which melts or liquefies upon heating to a higher temperature. Upon cooling, the material solidifies or returns to a solid or semi-solid state. As also used in this description, the term "hot-melt adhesive" is a term which is well known in the art, which material has the same characteristics of liquefaction upon heating and, upon cooling, solidification to a solid, semi-solid, or tacky state. Hot-melt adhesives are typically melted or liquefied to cause flow and then solidified upon cooling after contacting an adherend (i.e., substrate), generally under moderate pressure.

Examples of thermoplastic materials include polymers of ethylenically unsaturated monomers such as polyethylene, polypropylene, polystyrenes, polyvinyl chloride, polyvinyl acetate, polymethyl methacrylate, polyethyl acrylate, polyacrylonitrile, and the like; copolymers of ethylenically unsaturated monomers such as copolymers of ethylene and propylene, styrene, or polyvinyl acetate; styrene and maleic anhydride, methyl methacrylate, ethyl acrylate, or acrylonitrile; methyl methacrylate and ethylacrylate; and the like; polymers and copolymers of conjugated dienes such as polybutadiene, polyisoprene, polychloroprene, styrenebutadiene rubber, ethylene-propylene-diene rubber, acrylonitrile-styrene butadiene rubber and the like; saturated and unsaturated polyesters including alkyds and other polyesters; nylons and other polyamides; polyesteramides and polyurethanes; chlorinated polyethers; epoxy polymers; and cellulose esters such as cellulose acetate butyrate, and the like. Blends of thermoplastic materials can also be used, including, but not limited to, physical mixtures and copolymers. Particularly suitable thermoplastic materials include polyethylene, polypropylene, polyesters, ethylene vinyl acetate, and blends thereof.

Hot-melt adhesives are typically based on one or more types of thermoplastic materials, such as those described above. Thus, the hot-melt adhesives used herein may be a thermoplastic material or a composition comprising a thermoplastic material. The various hot-melt adhesives known in the art are suitable for use herein.

The thermoplastic material is preferably elastomeric. Elastomeric materials are believed to be particularly useful for maintaining the integrity of the absorbent core while the absorbent core is subjected to flexural or torsional forces such as encountered in use. More particularly, elastomeric adhesives are believed to have better adhesion to the absorbent article components than non-elastomeric adhesives, particularly under the dynamic conditions encountered in use of the absorbent article By "elastomeric," "elastic," etc it is meant that the material is able to be stretched to at least twice its original length and to retract to approximately its original length when released. Exemplary elastomeric, hot-melt adhesives include thermoplastic elastomers such as ethylene vinyl acetates, polyurethanes, polyolefin blends of a hard component (generally a crystalline polyolefin such as polypropylene or polyethylene) and a soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers; mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprene-styrene block copolymer with polystyrene; and the elastomeric, hot-melt, pressure-sensitive adhesives described herein. Elastomeric, hot-melt adhesives of these types are described in more detail in U.S. Pat. No. 4,731,066 issued to Korpman on Mar. 15, 1988, which is incorporated herein by reference.

Preferred hot-melt adhesives for forming the primary core integrity layer are hot-melt, pressure-sensitive adhesives. Hot-melt, pressure-sensitive adhesives, as understood by those of ordinary skill in the art, have some degree of surface tack at use temperatures. These tacky materials typically have a viscosity at room temperature (about 20° C. to about 25° C.) which is sufficiently low to permit good surface contact yet high enough to resist separation under stress, typically on the order of $10^4$–$10^6$ centipoise. Due to their surface tack, the pressure-sensitive adhesives used herein tend to increase the coefficient of friction between absorbent article components which may be adjacent to the pressure-sensitive adhesive, for example, the absorbent core layers. In addition, the pressure-sensitive adhesives provide manufacturing flexibility since joinder of the primary core integrity layer to other absorbent article components may then occur via the pressure-sensitive properties of the adhesive after the adhesive has solidified. Various hot-melt, pressure-sensitive adhesives are known in the art and are suitable for use herein.

Preferred hot-melt, pressure-sensitive adhesives are also elastomeric. Elastomeric, hot-melt, pressure-sensitive adhesives are disclosed in the above referenced and incorporated U.S. Pat. No. 4,731,066, and include those materials based on thermoplastic block copolymers, polyacrylates, and ethylene vinyl acetate. Suitable elastomeric, hot-melt, pressure-sensitive adhesives include the A-B-A block copolymer based adhesives which are specified as H-2085 and H-2031 by Findley Adhesives, Inc., of Wauwatosa, Wis.

The primary core integrity layer can be formed using a meltblown fiber process. Meltblown fiber processes and equipment are generally known in the art. In general, the thermoplastic material is heated to and held at a temperature sufficient to allow meltblown processing, typically at least until the material is in a liquid or molten state (melt/liquefaction temperature). (In general, the selection of any given temperature in the meltblown process is limited by the degradation temperature of the particular thermoplastic material being processed.) The molten/liquefied material is extruded under pressure (gun pressure) through orifices in a meltblown glue gun. Upon extrusion, the molten/liquid material is subjected to air flowing under pressure (air pressure) which fiberizes the material (strands are formed). The meltblown glue gun and air are heated to a desired gun temperature and air temperature, respectively, in order to facilitate strand formation. During and/or after strand formation, the thermoplastic material cools to form stabilized strands of the thermoplastic material. The apparatus is configured such that the strands are laid onto a desired substrate.

In the present invention, the meltblown process parameters are preferably selected to provide a mesh having a certain strand orientation and denier. These parameters include the melt/liquefaction temperature, gun temperature, air pressure, and air temperature. In a preferred embodiment, these parameters are varied to enable the formation of sinuous (wavy) strands which are oriented in substantially the same direction with some crosswise linking to form an intertwining web of the strands. In addition, it is generally desired to form relatively large denier strands, since the degree of wetting of the thermoplastic material to the absorbent core and thus the degree of improvement in absorbent core integrity tends to increase with increasing strand denier. The strands preferably have a denier of at least about 60 microns, preferably from about 80 microns to about 200 microns, more preferably about 90 to about 200 microns, most preferably about 100 to about 200 microns.

In general, as the viscosity of the thermoplastic material being meltblown decreases, strand formation more readily occurs, with the resultant strands tending to have a finer denier. The viscosity also influences the strand orientation, the orientation tending to become more random with decreasing viscosity. The viscosity for a given material typically decreases with an increasing melt/liquefaction temperature and particularly with increasing gun temperature. Therefore, the melt/liquefaction and gun temperatures are selected to provide a viscosity which enables strand formation as desired.

The melt/liquefaction temperature is typically from about 121° C. (250° F.) to about 204° C. (400° F.), preferably about 149° C. (300° F.) to about 190° C. (375° F.).

The adhesives designated H-2031 and H-2085 are typically held at a temperature of from about 135° C. (275° F.) to about 204° C. (400° F.), preferably about 149° C. (300° F.) to about 177° C. (350° F.), more preferably about 165° C. (330° F.).

The gun temperature is typically at or above the melt/liquefaction temperature, preferably above the latter temperature in order to facilitate strand formation. The gun temperature is typically from about 149° C. (300° F.) to about 204° C. (400° F.), preferably about 163° C. (325° F.) to about 190° C. (375° F.), more preferably about 182° C. (360° F.).

The air pressure influences both strand orientation and denier. For a given material and set of process temperatures (particularly gun and air temperatures), as the air pressure increases the strands tend to form in a more random orientation and with a finer denier. The air pressure is preferably at least high enough to form strands of molten/liquefied thermoplastic material which touch and thus are able to interconnect while the thermoplastic material is in a sufficiently molten/liquid state, as described below. In a preferred embodiment, the air pressure is selected to enable the formation of sinuous strands in substantially the same direction with some crosswise linking to form an intertwining web of strands. Thus, it is preferred that the air pressure is not so high as to cause the formation of strands in random orientation. Typically, the air pressure is from about 4 psi to about 15 psi, preferably about 6 to about 10 psi, more preferably about 7 to about 9 psi, most preferably about 8 psi.

The air temperature will generally be selected so as to maintain the extruded thermoplastic material in the molten/liquefied state. Thus, the air temperature will usually be greater than or equal to the gun temperature in order to offset any cooling effects which might otherwise occur. Preferably, the air temperature is sufficient to ensure the interconnection of the individual strands of thermoplastic material on the substrate (although the extruded material need not be in the same melt/liquefaction state as when first extruded, it is preferably sufficiently molten/liquefied to enable interconnection of the strands). Typically, the air temperature is from about 204° C. (400° F.) to about 238° C. (460° F.), preferably from about 215° C. (420° F.) to about 227° C. (440° F.), more preferably about 221° C. (430° F.). Upon cooling to a temperature sufficient to resolidify the thermoplastic material, the resultant mesh of interconnected strands is stabilized.

The thermoplastic material is applied to the substrate (e.g., an absorbent core component) so as to not interfere substantially with absorption of the absorbent core. Thus, the basis weight of the mesh of thermoplastic material is typically from about 2 to about 8 grams/square meter (g/m$^2$), preferably about 3 to about 7 g/m$^2$, more preferably about 4 to about 6 g/m$^2$, most preferably about 5 g/m$^2$.

The particular meltblown equipment used herein is typically selected according to the width of the absorbent core (or absorbent core component) which is to be enveloped. In general, the equipment is selected which will provide, in one step, a width of mesh of thermoplastic material which is sufficient to envelope the absorbent core. (Where a, primary core integrity layer or secondary core integrity layer as described herein is not intended to envelope at least a portion of the side edges of an absorbent core component, the meltblown glue gun is selected to provide a mesh width which is smaller than the width of the absorbent core component). For the absorbent articles herein, a 2 module, 3.0" width meltblown glue gun designated AMBI-3.0-2 and a 4 module, 6" width meltblown glue gun designated AMBI-6.0-4, each available from J and M Laboratories of Dawsonville, Ga., are suitable for use.

The primary core integrity layer is preferably formed by the meltblown process in a continuous process (online) during manufacture of the absorbent article. Alternatively, the primary core integrity layer may be formed by the above meltblown process or by conventional methods in an intermediate process for later incorporation into the absorbent article. Thus, the primary core integrity layer may be a preformed, nonwoven, fluid pervious web comprising strands of thermoplastic material. However, since the use of preformed non-wovens tends to add to the ultimate cost of the absorbent article, this alternative is not preferred.

As described above, the primary core integrity layer is preferably positioned such that it envelopes the absorbent core. The primary core integrity layer is also joined to at least one of the chassis components (e.g., the topsheet and backsheet) of the diaper 20. In a preferred embodiment, the primary core integrity layer is directly joined to a chassis component, preferably the topsheet. The primary core integrity layer can be joined to a chassis component by a construction adhesive. Alternatively, the primary core integrity layer may be joined to a chassis component by the hot-melt or pressure-sensitive properties of the thermoplastic material of the primary core integrity layer, where such materials are used.

In a preferred embodiment, the primary core integrity layer is directly joined to the chassis component by a construction adhesive. It is believed that such joinder tends to form a higher strength bond than if the primary core integrity layer is bonded directly to the chassis component via the hot-melt or pressure-sensitive properties of the primary core integrity layer material and without any construction adhesive, such that the absorbent core integrity is enhanced. It is further believed that this bond strength will be higher where the construction adhesive material is the same as the material used to form the primary core integrity layer; for this reason this embodiment is more preferred. However, for economic reasons, it may not be desirable to use the same types of materials for the construction adhesive and the primary core integrity layer.

Suitable construction adhesives include any of the adhesive materials such as are known in the art of bonding absorbent cores to chassis components, including those described herein in reference to joining the backsheet and the absorbent core. The construction adhesive can comprise any of the hot-melt adhesives described in reference to the thermoplastic materials for forming the primary core integrity layer.

The construction adhesive can be applied to a given substrate (e.g., the primary core integrity layer, an absorbent core component, or a chassis component) by conventional methods such as described herein in reference to joinder of the backsheet and absorbent core. Preferably, the construction adhesive is applied in an open pattern of construction adhesive. As used herein, "open pattern of construction adhesive" means that the construction adhesive is present on a substrate in a pattern which allows for relatively unimpeded fluid transport into and/or through the absorbent core. Suitable open patterns and methods of making the same are disclosed in the above referenced U.S. Pat. Nos. 4,573,986; 3,911,173; 4,785,996; and 4,842,666. Thus, the open pattern of construction adhesive may comprise a fine pattern of globulettes of construction adhesive or reticulated networks of filaments of construction adhesive, including spiral and/or bead patterns. The globulettes and filaments may have diameters about equal in order of magnitude to the effective average diameter of the fibers which constitute the absorbent core. The construction adhesive may also be applied by a meltblown process, including the process described for making the primary core integrity layer.

Joinder of the primary core integrity layer to a chassis component via the hot-melt properties of the primary core integrity layer material will typically be effected using a continuous process in which the primary core integrity layer is formed and joined to a chassis at substantially the same time, during construction of the absorbent article. Thus, while the thermoplastic, hot-melt material of the primary core integrity layer is still in a liquefied/molten state sufficient to enable joinder, pressure is applied to the structures being joined in order to ensure good contact and adhesion between the primary core integrity layer and the chassis component. As will be recognized by those skilled in the art, the process temperature and thus suitable thermoplastic materials should be selected to avoid damage to the chassis component. Joinder of a primary core integrity layer formed of a hot-melt, pressure-sensitive material can be effected in a like manner or, alternatively, via the pressure-sensitive properties of the thermoplastic material after solidification of the material. For a primary core integrity layer formed of a pressure-sensitive material, pressure may alternatively be applied after the pressure-sensitive adhesive material of the primary core integrity layer has solidified.

In joining the primary core integrity layer to the chassis, it will usually be desired to minimize the pressure on the absorbent core during joinder in order to optimize the absorbent core integrity. In conventional diaper converting lines, the pressure can be minimized, for example, by using a combining roll which has a pattern corresponding to the shape of the absorbent core and/or by varying the clearance between the combining rolls.

In a preferred embodiment, the absorbent core comprises at least one additional core integrity layer, a secondary core integrity layer, positioned between various absorbent layers, preferably webs or batts, of the absorbent core. (As should be understood by those of ordinary skill in the art, such absorbent layers may, like the absorbent core, have a garment facing surface, body facing surface, side edges, and end edges.) The secondary core integrity layer in preferred absorbent articles will thus be positioned between the primary core integrity layer and the chassis component to which the primary core integrity layer is joined. (However, where the primary core integrity layer envelopes only a portion of the absorbent core layers, a secondary core integrity layer may be positioned between absorbent core layers which are not enveloped by the primary core integrity layer.) The secondary core integrity layer comprises a continuous mesh of thermoplastic material, as defined in reference to the primary core integrity layer. The secondary core integrity layer is joined to a chassis component and may be directly joined thereto, e.g., where the secondary core integrity layer envelopes the absorbent core layers positioned between the secondary core integrity layer and the chassis.

The secondary core integrity layer may or may not envelope one or more absorbent layers of the absorbent core as described for the primary core integrity layer. It is believed that, in order to maximize absorbent core integrity, each secondary core integrity layer should envelope the absorbent core layers which are positioned between the secondary core integrity layer and the chassis component to which the primary core integrity layer and/or secondary core integrity layer is joined. However, certain absorbent article configurations may not readily allow such enveloping, particularly as formed on commercial converting equipment. As shown in FIG. 2, the surface area of the secondary core integrity layer 140 is less than the surface areas of each of the various absorbent layers of the absorbent core (more specifically, the (lateral) width of the secondary core integrity layer 140 is less than the (lateral) widths of each of the acquisition/distribution layer 150, tissue layer 170, and storage layer 190). Thus, the secondary core integrity layer 140 does not envelope the side edges 152, 172, and 192 of, respectively, acquisition/distribution layer 150, tissue layer 170, and storage layer 190.

The secondary core integrity layer can alternatively envelope the absorbent layers as described for the primary core integrity layer. The extent of enveloping can be the same or different from that of the primary core integrity layer or any other secondary core integrity layer. Thus, the secondary core integrity layer can envelope relatively different longitudinal portions of the side edges of an absorbent layer, and/or a different surface and/or relative portion of a surface of an absorbent layer.

The secondary core integrity layer can be formed of a thermoplastic material and by a process as described for the primary core integrity layer. The secondary core integrity layer can be formed of the same thermoplastic material as the primary core integrity layer or from a different thermoplastic material. For ease of processing, the secondary core integrity layer is preferably formed of the same thermoplastic material as is the primary core integrity layer. In addition, the secondary core integrity layer can be formed using process parameters which are the same or different from those used to form the primary core integrity layer. Preferably, the same process parameters are used such that the secondary core integrity layer has a basis weight, and the strands of thermoplastic material thereof have a denier and orientation, which are substantially the same as the primary core integrity layer.

The secondary core integrity layer can be joined to one or more absorbent core layers and/or a chassis component. Joinder can occur using a construction adhesive and/or by the hot-melt and/or pressure-sensitive properties of the secondary core integrity layer material, as described for joinder of the primary core integrity layer to a chassis component.

The structure shown in FIG. 3 can be formed in the following manner. A secondary core integrity layer 140 0 is formed on the garment facing surface of acquisition/distribution layer 150. The secondary core integrity layer 140 is joined to tissue layer 170 by construction adhesive layer 92 which is preferably applied to the body facing surface of tissue layer 170. The garment facing surface of tissue layer 170 is then joined to storage layer 190 by construction adhesive layer 94 which is preferably applied to the garment facing surface of tissue layer 170. The resultant laminate is then joined to the topsheet 24 by construction adhesive layer 90, which joins the acquisition/distribution layer 150 to topsheet 24. The primary core integrity layer 120 is formed on the garment facing surface of storage layer 190, a portion of the garment facing surface of tissue layer 170 (corresponding to the differential lateral distance between side edges 192 of the storage layer 190 and the side edges 172 of tissue layer 170), and a portion of the garment facing surface of topsheet 24 (corresponding to the differential lateral distance between the side edges 172 of tissue layer 170 and the side edges 122 of the primary core integrity layer 120). The backsheet 26 is then joined to the primary core integrity layer 120 by construction adhesive layer 96 and to the topsheet 24 by a construction adhesive (not shown).

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) The elasticized leg cuffs 32 can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989. In a preferred embodiment, each elasticized leg cuff 32 comprises at least an inner barrier cuff comprising a barrier flap and a spacing elastic member such as described in U.S. Pat. No. 4,909,803. In another preferred embodiment, the elasticized leg cuff additionally comprises an elastic gasketing cuff with one or more elastic strands positioned outboard of the barrier cuff such as described in U.S. Pat. No. 4,695,278.

The diaper 20 preferably further comprises an elastic waist feature 34 that provides improved fit and containment. The elastic waist feature 34 is that portion or zone of the diaper 20 which is intended to elastically expand and contract to dynamically fit the wearer's waist. The elastic waist feature 34 at least extends longitudinally outwardly from at least one of the end edges 83 of the absorbent core 28 and generally forms at least a portion of the end edge 64 of the diaper 20. Disposable diapers are generally constructed so as to have two elastic waist features, one positioned in the first waist region and one positioned in the second waist region, although diapers can be constructed with a single elastic waist feature. Further, while the elastic waist feature or any of its constituent elements can comprise a separate element affixed to the diaper 20, the elastic waist feature 34 is preferably constructed as an extension of other elements of the diaper such as the backsheet 26 or the topsheet 24, preferably both the backsheet 26 and the topsheet 24.

The elasticized waistband 35 of the elasticized waist feature 34 may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

In a preferred embodiment, the diaper also comprises elasticized side panels 30 disposed in the second waist region 58. (As used herein, the term "disposed" is used to mean that an element(s) of the diaper is formed (joined and positioned) in a particular place or position as a unitary structure with other elements of the diaper or as a separate element joined to another element of the diaper.) The elasticized side panels 30 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract. The elasticized side panels 30 further provide more effective application of the diaper 20 since even if the diaperer pulls one elasticized side panel 30 farther than the other during application (asymmetrically), the diaper 20 will "self-adjust" during wear. While the diaper 20 of the present invention preferably has the elasticized side panels 30 disposed in the second waist region 58; alternatively, the diaper 20 may be provided with elasticized side panels 30 disposed in the first waist region 56 or in both the first waist region 56 and the second waist region 58. While the elasticized side panels 30 may be constructed in a number of configurations, examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference. As shown in FIG. 1, each elasticized side panel 30 preferably comprises an ear flap 88 and an elastic side panel member 90 operatively associated therewith, such as described in U.S. Pat. No. 5,151,092.

The diaper 20 also comprises a fastening system 36 which forms a side closure which maintains the first waist region 56 and the second waist region 58 in an overlapping configuration such that lateral tensions are maintained around the circumference of the diaper to maintain the diaper on the wearer. Exemplary fastening systems are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. B1 4,662,875, issued to Hirotsu et al. on May 5, 1987; and U.S. Pat. No. 5,151,092, issued to Buell et al. on Sep. 29, 1992; each of which is incorporated herein by reference. In a preferred embodiment, the fastening system comprises a dual tension fastening system comprising a primary fastening system and a waist closure system as described in U.S. Pat. No. 5,151,092.

The diaper 20 is preferably applied to a wearer by positioning one of the waist regions, preferably the second waist region 58, under the wearer's back and drawing the remainder of the diaper between the wearer's legs so that the other waist region, preferably the first waist region 56, is positioned across the front of the wearer. The tape tabs of the fastening system are then released from the release portion. The diaperer then wraps the elasticized side panel around the wearer, while still grasping the tab portion. The elasticized side panels will typically be extended and tensioned during this operation so as to conform to the size and shape of the wearer. The fastening system is secured to the outer surface of the diaper to effect a side closure.

EXAMPLE I

A disposable diaper can be prepared comprising a thermally bonded polypropylene topsheet, a fluid impervious polyethylene backsheet and an absorbent core positioned between the topsheet and the backsheet, in which the absorbent core is enveloped by a primary core integrity layer which is directly joined to the topsheet and the backsheet, in the following manner. The absorbent core will comprise a modified hourglass-shaped storage layer positioned below a substantially rectangular-shaped acquisition/distribution layer and a rectangular-shaped, liquid pervious, wet-strength tissue sheet positioned therebetween. A secondary core integrity layer will be positioned between the acquisition/distribution layer and the tissue layer.

The acquisition/distribution layer is an air laid web of stiffened, twisted, curled cellulose fibers. The stiffened, twisted, curled cellulosic fibers are made from Foley fluff (southern softwood kraft pulp, Buckeye Cellulose Corp., Memphis, Tenn., USA) having a moisture content of about 7%. The Foley fluff fibers are crosslinked with citric acid to the extent of about 3.8 mole percent citric acid on a dry fiber cellulose anhydroglucose basis. The fibers are crosslinked by a dry crosslinking process as described in U.S. Pat. No. 5,137,537, issued to Herron et al. on Aug. 11, 1992. The fibers are airlaid to form a uniform web which is compressed with a hydraulic press to a density of 0.20 g/cc.

The storage layer comprises an air laid mixture of Foley fluff and sodium polyacrylate polymeric absorbent gelling material particles of the type described in U.S. Pat. No. RE 32,649, reissued Apr. 19, 1988, and having an Absorbent Capacity of about 28 g/g. The storage layer has a fill layer which is a mixture of about 40% Foley fluff and about 60% absorbent gelling material which will be positioned adjacent the garment facing side of the tissue, and a dusting layer consisting essentially of the Foley fluff adjacent the fill layer. The fill layer has a width of about 10.7 cm (4.2") along the length of the storage layer. The storage layer comprises about 50% by weight Foley fluff and about 50% by weight absorbent gelling material.

The acquisition/distribution layer has dimensions (width X length) of about 8.9 cm (3.5") (in the crotch region) by about 38.7 cm (15.25") and is positioned relative to the storage layer as shown in FIGS. 2 and 3. The storage layer has a minimum crotch width of about 10.7 cm (4.2"), a width at the ears of about 19.1 cm (7.5"), and a width at the rear (back) waist area of about 12.2 cm (4.8"). The tissue layer has dimensions of about 14.7 cm (5.8") X about 38.7 cm (15.25").

A secondary core integrity layer will be formed on the acquisition/distribution layer by applying the adhesive H-2085 (Findley Adhesives, Inc.) directly onto the garment facing side of the acquisition/distribution layer using a J and M Laboratories 7.62 cm (3.0") meltblown glue gun designated AMBI-3.0-2 at an air pressure of 8 psi. (In forming each of the meltblown layers in this example, the meltblown adhesive materials are held at a temperature of 165° C. (330° F.); the gun temperature is 182° C. (360° F.); and the air temperature is 221° C. (430° F.)). The H-2085 adhesive is applied at a basis weight of 3.23 mg/in². A mesh is thus formed on the acquisition/distribution layer in the form of sinuous (wavy) strands of the H-2085 adhesive which are oriented in substantially the same direction with some crosswise linking so as to be intertwined. The strands have a denier of about 100 microns. The secondary core integrity layer will then be joined to the tissue layer by a layer of meltblown HL-1258 adhesive (H.B. Fuller Co.) which is applied to the tissue. The meltblown HL-1258 adhesive is applied to the tissue using a J and M Laboratories AMBI-3.0-2 meltblown glue gun with an air pressure of 20 psi at a basis weight of 3.1 mg/in$^2$. The resultant strands will have a denier of about 25 microns. The tissue layer will then be joined to the storage layer by meltblown HL-1258 adhesive applied to the garment facing side of the tissue. The meltblown HL-1258 adhesive is applied to the garment facing side of the tissue using a J and M Laboratories 11.43 cm (4.5") meltblown glue gun designated AMBI-4.5-3 with an air pressure of 20 psi at an HL-1258 adhesive basis weight of 2.1 mg/in$^2$; the resultant strands will have a denier of about 25 microns. The body facing side of the acquisition/distribution layer will then be joined to the topsheet using a spiral pattern of the adhesive HL-1258 applied to the topsheet. 6 spirals are applied to the topsheet, the spirals having a width of 0.8" and 0.875" centers such that the HL-1258 adhesive has a basis weight of 2.00 mg/in$^2$. A primary core integrity layer of meltblown H-2085 adhesive will then be formed on the storage layer using a J and M Laboratories 15.24 cm (6.0") meltblown glue gun designated AMBI-6.0-4 with an air pressure of 8 psi at an H-2085 adhesive basis weight of 2.42 mg/in$^2$. The resultant mesh will be in the form of sinuous (wavy) strands of the H-2085 adhesive which are oriented in substantially the same direction with some crosswise linking so as to be intertwined. The strands have a denier of about 100 microns. The primary core integrity layer will then be joined to the backsheet by fourteen (14) HL-1258 adhesive beads at an HL-1258 adhesive basis weight of 1.28 mg/in$^2$ and by meltblown HL-1258 adhesive at a basis weight of 3.85 mg/in$^2$. The meltblown HL-1258 adhesive is applied using a J and M Laboratories AMBI-6.0-4 meltblown glue gun with an air pressure of 20 psi (strand denier will be about 25 microns); the HL-1258 adhesive beads are applied using a bead extruder. The primary core integrity layer will then be joined to the topsheet by HL-1258 adhesive applied to the topsheet. The topsheet and backsheet will then be joined by HL-1258 adhesive applied to the backsheet. The finished diaper will be packaged using a compressive force bagger with a compressive force of 1200 psi. The caliper of the finished diaper will be about 0.53 cm (0.21").

EXAMPLE 2

A diaper can be prepared as in Example 1 except that the fill layer has a basis weight gradient. The fill layer comprises about 15% of the absorbent gelling material particles and about 80 to 85% of Foley fluff and has a basis weight gradient such that the front 60% of the storage layer has a basis weight of about 0.10–0.15 g/cm$^2$ (preferably 0.11 g/cm$^2$) and a density of about 0.13–0.20 g/cc (preferably 0.15 g/cc) and the rear 40% of the storage layer has a basis weight of about 0.03–0.05 g/cm$^2$ (preferably 0.04 g/cm$^2$) and a density of about 0.05–0.20 g/cc (preferably 0.06 g/cc). This storage layer is particularly useful as an absorbent core without an acquisition/distribution layer.

EXAMPLE 3

A diaper can be made as in Example 2, except that the storage layer will have about 28% of the absorbent gelling material particles and about 72% of Foley fluff. The storage layer has a basis weight gradient as described in Example 2.

EXAMPLES 4–6

Examples 4–6 can be made in the same manner as Examples 1–3, except that the bagger force is 700 psi.

Examples 1–6 would exhibit improved absorbent core integrity, including reduced slumping, reduced roping, and reduced tearing in the crotch region (both along the lateral crotch fold lines and elsewhere), particularly tearing of the acquisition/distribution layer. This absorbent core integrity improvement leads to increased absorbent core utilization, particularly since diapers containing acquisition/distribution layers torn in the fold area have a lower probability of containing urine past the fold line than diapers that are not torn. Examples 4–6, using a lower bagger force, would tend to show the most improvement in absorbent core integrity, particularly a reduction in tearing along the lateral crotch fold line of the diapers.

The absorbent core integrity is determined by tearing grade, roping grade, and percent urine past fold line. These in turn are evaluated by comparing a dry diaper to a diaper wetted in actual use only by urine of a known urine loading.

The roping grade is determined by visually inspecting the absorbent core crotch region using a "light box" such as are known in the art. The absorbent core width of the used diaper is compared to that of the unused diaper. A negative change in width after use may be indicative of some degree of roping, with greater negative changes indicating higher degrees of roping. The change in width is apparent by bunching of the absorbent core. The bunching results in a change in softness and/or stiffness of the absorbent core as a result of packing/matting of the absorbent core material. The absorbent cores are graded on a scale of 1–4 as follows:
1. Severe bunching—absorbent core is hard and stiff.
2. Moderate bunching—absorbent core is hard but still pliable.
3. Slight bunching—absorbent core starts to mat.
4. No roping.

Absorbent core tearing grade is determined by visual inspection of the entire absorbent core for cracks and tears. The more tears, the lower the grade, with all tears in the crotch area being weighted more heavily than tears outside the crotch area. The absorbent cores are graded on a scale of 1–4 as follows:
1. Severe tearing—tears separate the crotch along the lateral fold line and/or are longer than 6 cm outside the crotch area.
2. Moderate tearing—tears half separate the crotch along the lateral fold line and/or are between 3 and 6 cm long outside the crotch area.
3. Slight tearing—tears in the crotch are less than 2 cm long and less than 3 cm outside the crotch area.
4. No tears.

The percent of urine past fold line is indicative of breakage of the absorbent core in the region of the lateral crotch fold line. This percentage is determined by cutting the wetted diaper along the fold line. The rear portion (worn toward the back of the wearer's body) is weighed. The weight of the rear portion is divided by the weight of the entire wetted diaper and multiplied by 100 to obtain the percent urine past fold line.

Absorbent core slumping is indicative of slippage between, and/or separation of, the absorbent core (or component thereof) and a chassis component (and/or another absorbent core component). Slumping may indicate a loss of adhesion between a fibrous absorbent core component and the glue bonding the fibrous component to the topsheet or to another fibrous absorbent core component. Slumping is determined visually by using a "light box."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a) a liquid pervious topsheet;
   b) a liquid impervious backsheet joined to said topsheet;
   c) an absorbent core positioned between said topsheet and said backsheet, said absorbent core having a garment facing surface, a body facing surface, and side edges; and
   d) a primary core integrity layer enveloping at least a longitudinal portion of said side edges and at least a portion of one of said surfaces, said primary core integrity layer being joined to said topsheet, said primary core integrity layer comprising a continuous mesh of strands of meltblown material, said strands being sinuous and oriented in substantially the same direction with some crosswise linking to form an intertwining web of the strands.

2. The absorbent article of claim 1 wherein said primary core integrity layer is directly joined to said topsheet.

3. The absorbent article of claim 2 wherein said primary core integrity later envelopes at least a portion of said garment facing surface of said absorbent core.

4. The absorbent article of claim 3 wherein said absorbent core comprises an upper acquisition/distribution layer and a lower storage layer.

5. The absorbent article of claim 4 additionally comprising a secondary core integrity layer comprising a continuous mesh of strands of meltblown material positioned between said acquisition/distribution layer and said storage layer, said strands of said secondary core integrity layer being sinuous and oriented in substantially/the same direction with some crosswise linking to form an intertwining web of the strands.

6. The absorbent article of claim 5 wherein the surface area of said secondary core integrity layer is less than or equal to the surface areas of both said acquisition/distribution layer and said storage layer.

7. The absorbent article of claim 6 wherein said absorbent core additionally comprises a tissue layer positioned between said secondary core integrity layer and said storage layer.

8. The absorbent article of claim 7 wherein the surface area of said secondary core integrity layer is less than or equal to the surface area of said tissue layer.

9. The absorbent article of claim 1 or 5 wherein said strands of both said primary core integrity layer and said secondary core integrity layer have a denier of at least about 60 microns.

10. The absorbent article of claim 9 wherein both said primary core integrity layer and said secondary core integrity layer have a basis weight of about 2 g/m$^2$ to about 8 g/m$^2$.

11. The absorbent article of claim 10 wherein said meltblown material is a hot-melt, elastomeric, pressure-sensitive adhesive.

12. An absorbent article comprising:
   a) a liquid pervious topsheet;
   b) a liquid impervious backsheet joined to said topsheet;
   c) an absorbent core positioned between said topsheet and said backsheet, said absorbent core comprising:
      (i) an acquisition/distribution layer comprising chemically stiffened, twisted, curled, intrafiber-crosslinked cellulosic fibers;
      (ii) a storage layer comprising a mixture of absorbent gelling material and cellulosic fibers; and
      (iii) a tissue layer positioned between said acquisition/distribution layer and said storage layer;
      said acquisition/distribution layer, tissue layer, and storage layer each having an upper surface, a lower surface, and side edges; said absorbent core having a body facing surface formed by said upper surface of said acquisition/distribution layer, a garment facing surface formed by said lower surface of said storage layer, and side edges;
   d) a primary core integrity layer enveloping at least a longitudinal portion of said side edges of each of said layers of said absorbent core and at least a portion of said garment facing surface of said absorbent core, said primary core integrity layer being joined to said topsheet, said primary core integrity layer comprising a continuous mesh of strands of meltblown material, said strands being sinuous and oriented in substantially the same direction with some crosswise linking to form an intertwining web of the strands; and
   e) a secondary core integrity layer comprising a continuous mesh of strands of meltblown material positioned between said acquisition/distribution layer and said tissue layer, said strands of said secondary core integrity layer being sinuous and oriented in substantially the same direction with some crosswise linking to form an intertwining web of the strands.

13. The absorbent article of claim 12 wherein the surface area of said secondary core integrity layer is less than or equal to the surface areas of both said acquisition/distribution layer and said tissue layer.

14. The absorbent article of claim 13 wherein said strands of meltblown material of both said primary core integrity layer and said secondary core integrity layer have a denier of at least about 60 microns.

15. The absorbent article of claim 14 wherein both said primary core integrity layer and said secondary core integrity layer have a basis weight of about 2 g/m$^2$ to about 8 g/m$^2$.

16. The absorbent article of claim 15 wherein said meltblown material is a hot-melt, elastomeric, pressure-sensitive adhesive.

* * * * *